(12) United States Patent
Goldstein et al.

(10) Patent No.: US 8,326,412 B2
(45) Date of Patent: Dec. 4, 2012

(54) DIAGNOSTIC DEVICE AND METHOD FOR SENSING HYDRATION STATE OF A MAMMALIAN SUBJECT

(75) Inventors: Andrew S. Goldstein, Portland, OR (US); Frank Bellizzi, San Francisco, CA (US)

(73) Assignee: HydraDx, Inc., Altadena, CA (US)

( * ) Notice: Subject to any disclaimer, the term of this patent is extended or adjusted under 35 U.S.C. 154(b) by 22 days.

(21) Appl. No.: 13/249,521

(22) Filed: Sep. 30, 2011

(65) Prior Publication Data

US 2012/0083711 A1 Apr. 5, 2012

Related U.S. Application Data

(63) Continuation of application No. PCT/US2011/054104, filed on Sep. 29, 2011.

(60) Provisional application No. 61/450,977, filed on Mar. 9, 2011, provisional application No. 61/388,234, filed on Sep. 30, 2010.

(51) Int. Cl.
 *A61B 5/05* (2006.01)
(52) U.S. Cl. .................. 600/547; 600/345; 600/349
(58) Field of Classification Search ................ 73/1.16; 600/345, 349, 547
 See application file for complete search history.

(56) References Cited

U.S. PATENT DOCUMENTS

| | | | |
|---|---|---|---|
| 4,160,008 A | 7/1979 | Fenocketti et al. | |
| 4,568,534 A | 2/1986 | Stier et al. | |
| 5,334,502 A | 8/1994 | Sangha | |
| 5,580,794 A | 12/1996 | Allen | |
| 5,622,871 A | 4/1997 | May et al. | |
| 5,714,389 A | 2/1998 | Charlton et al. | |
| 6,485,982 B1 | 11/2002 | Charlton | |
| 6,998,273 B1 | 2/2006 | Fleming et al. | |
| 7,018,847 B2 | 3/2006 | Mendel-Hartvig et al. | |
| 7,192,555 B2 | 3/2007 | Mink et al. | |
| 2004/0082878 A1 | 4/2004 | Baldwin et al. | |
| 2006/0121548 A1 | 6/2006 | Robbins et al. | |
| 2006/0127961 A1 | 6/2006 | Gregory | |
| 2006/0278156 A1 | 12/2006 | Miller | |
| 2007/0048224 A1 | 3/2007 | Howell et al. | |
| 2007/0116597 A1 | 5/2007 | Mink et al. | |
| 2008/0050451 A1 | 2/2008 | Mabry | |
| 2008/0177166 A1 | 7/2008 | Pronovost et al. | |
| 2008/0274495 A1 | 11/2008 | Jumonville et al. | |
| 2010/0159611 A1 | 6/2010 | Song et al. | |
| 2010/0174156 A1 | 7/2010 | Patel et al. | |
| 2010/0330684 A1 | 12/2010 | O'Connor | |
| 2011/0287409 A1 | 11/2011 | O'Connor | |

OTHER PUBLICATIONS

Advice on Measuring SIgA in Saliva, Salimetrics, (available online at: http://gallery.mailchimp.com/d1503f81c39ca3c3897789a03/files/Measuring_SIgA.3.pdf).

(Continued)

*Primary Examiner* — Jeffrey G Hoekstra
*Assistant Examiner* — Charles Becker
(74) *Attorney, Agent, or Firm* — Vincent K. Gustafson; Jenkins, Wilson, Taylor & Hunt, P.A.

(57) ABSTRACT

Timed sensing of collection of saliva in a liquid collection element of predetermined volumetric capacity may be used to determine salivary secretion rate, as may be indicative of state of euhydration or dehydration. Sensing of salivary flow rate may be further augmented by sensing concentration of at least one analyte in saliva (e.g., with an immunochromatographic assay performed in a lateral flow device) in order to determine a state of euhydration or dehydration. Production of saliva may be stimulated, and collected saliva may be analyzed to generate an analyte detection signal that indicative of presence and/or correlative of concentration of at least one analyte in the collected saliva to sense a state of euhydration or dehydration.

26 Claims, 17 Drawing Sheets

OTHER PUBLICATIONS

Dezan, C. et al., "Flow rate, amylase activity, and protein and sialic acid concentrations of saliva from children aged 18, 30 and 42 month", "Archives of Oral Biology", 2002, pp. 423-427, vol. 47.

Dimitriou, I. et al., "CD40 on salivary gland epithelial cells: high constitutive expression by cultured cells from Sjogren's syndrome patients indicating their intrinsic activation ", "Clin. Exp. Immunol.", 2002, pp. 386-392, vol. 127.

Humphrey, S. et al., "A review of saliva: Normal composition, flow, and function", "J. Prosthetic Dent.", 2001, pp. 162-169, vol. 85.

Laing, S. J. et al., "Salivary IgA response to prolonged exercise in a hot environment in trained cyclists", "European Journal of Applied Physiology", Nov. 20, 2004, pp. 665-671, vol. 93.

Li, T. et al., "The effect of single and repeated bouts of prolonged cycling and circadian variation on saliva flow rate, immunoglobulin", "Journal of Sport Sciences", 2004, pp. 1015-1024, vol. 22.

Oliver, S. et al., "Saliva indices track hypohydration during 48 h of fluid restriction or combined fluid and energy restriction", "Archives of Oral Biology", 2008, pp. 975-980, vol. 53.

Ship, J. et al., "Metabolic indicators of hydration status in the prediction of parotid salivary gland function", "Achives of Oral Biology", 1999, pp. 343-350, vol. 44.

Walsh, N. et al., "The effects of high-intensity intermittent exercise on saliva IgA, total protein and a-amylase", "Journal of Sports Sciences", 1999, pp. 129-134, vol. 17.

Walsh, N. et al., "Saliva flow rate, total protein concentration and osmolality as potential markers of whole body hydration status . . . ", "Archives of Oral Biology", 2004, pp. 149-154, vol. 49.

Walsh, N. et al., "Saliva Parameters as Potential Indices of Hydration Status during Acute Dehydration", "Medicine and Science in Sports and Exercise", 2004, pp. 1535-1542, Publisher: American College of Sports Medicine.

Henskens, Y.M.C., et al., "Protein composition of whole and parotid saliva in healthy and periodontitis subjects", "Journal of Periodontal Research", 1996, pp. 57-65, vol. 31.

Nagler, R. M., et al., "Salivary gland involvement in rheumatoid arthritis and its relationship to induced oxidative stress", "Rheumatology", 2003, pp. 1234-1241, vol. 42.

Wu, Ava J., DDS, et al., "A characterization of major salivary gland flow rates in the presence of medications and systemic disease", "Oral Surgery Oral Medicine Oral Pathology", 1993, pp. 301-306, vol. 76.

Bookman, Arthur A. M., et al., "Whole Stimulated Salivary Flow: Correlation With the Pathology of Inflammation and Damage in Minor Salivary Gland Biopsy Specimens From Patients With Primary Sjogren's Syndrome but Not Patients With Sicca", Arthritis & Rheumatism, Jul. 2011, pp. 2014-2020, vol. 63, No. 7.

Navazesh, Mahvash, DMD, et al., "Measuring salivary flow. Challenges and opportunities", "The Journal of the American Dental Association", 2008, pp. 35S-40S, vol. 139.

Wolff, Andy, et al., "Submandibular and sublingual salivary gland function in familial dysautonomia," "Oral Surgery Oral Medicine Oral Pathology", Sep. 2002, pp. 315-319, vol. 94, No. 3.

Ghezzi, E.M., et al., "Determination of Variation of Stimulated Salivary Flow Rates", "Journal of Dental Research", 2000, pp. 1874-1878, vol. 11.

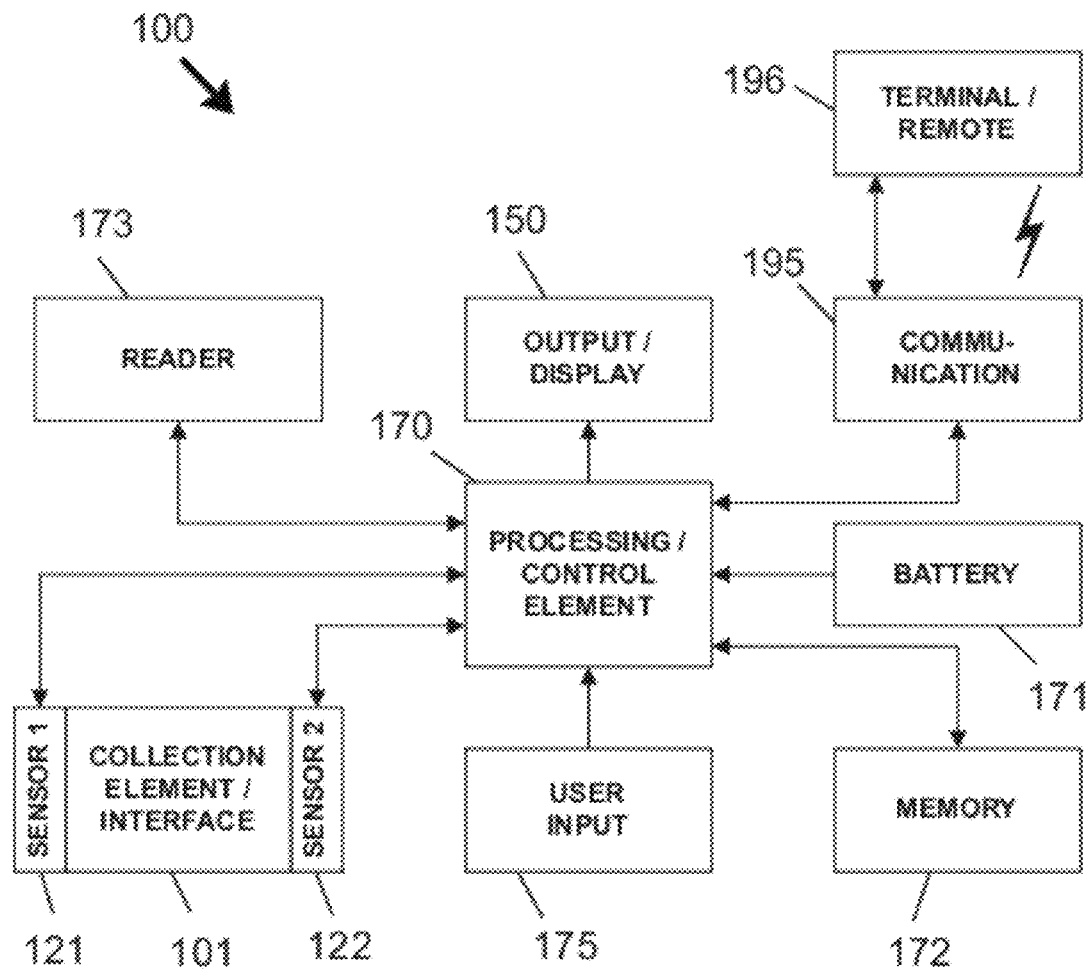
FIG._1

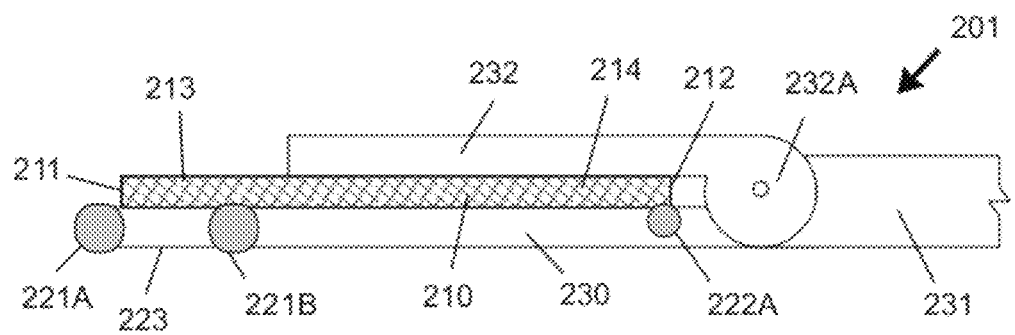
FIG._2
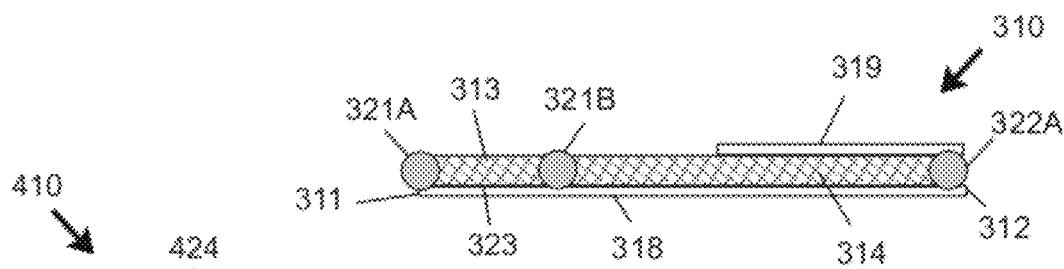
FIG._3
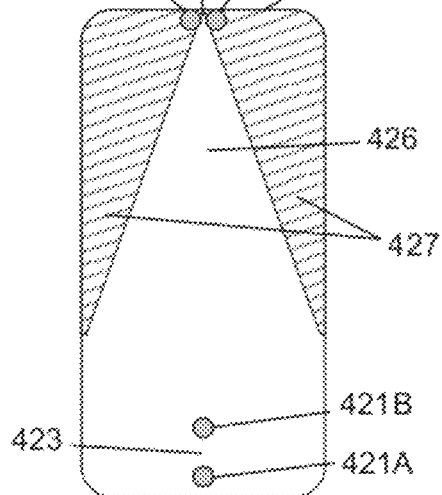
FIG._4

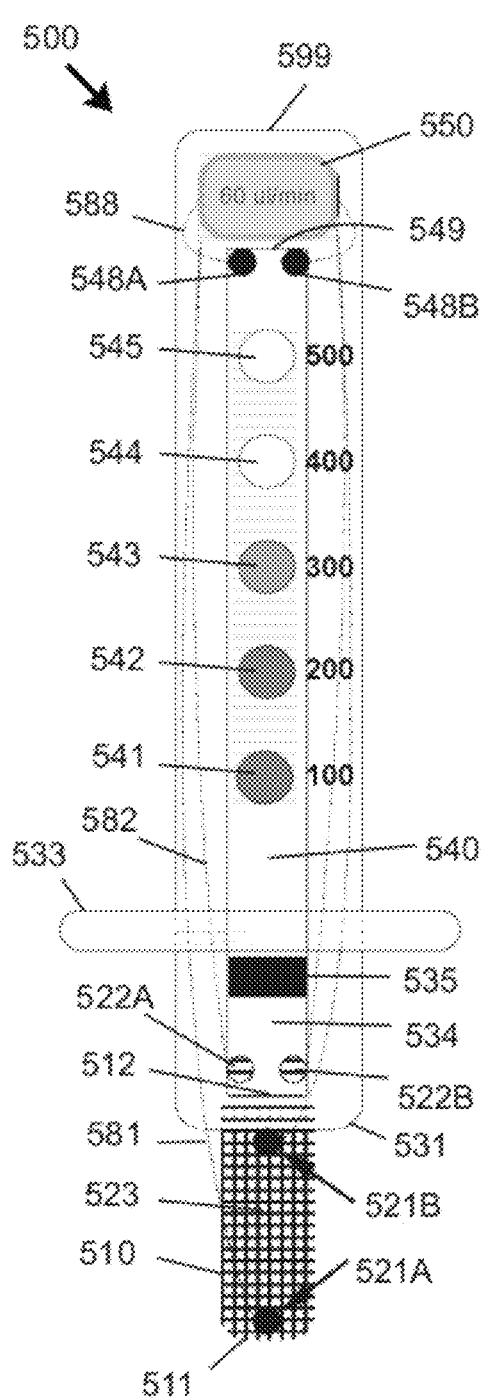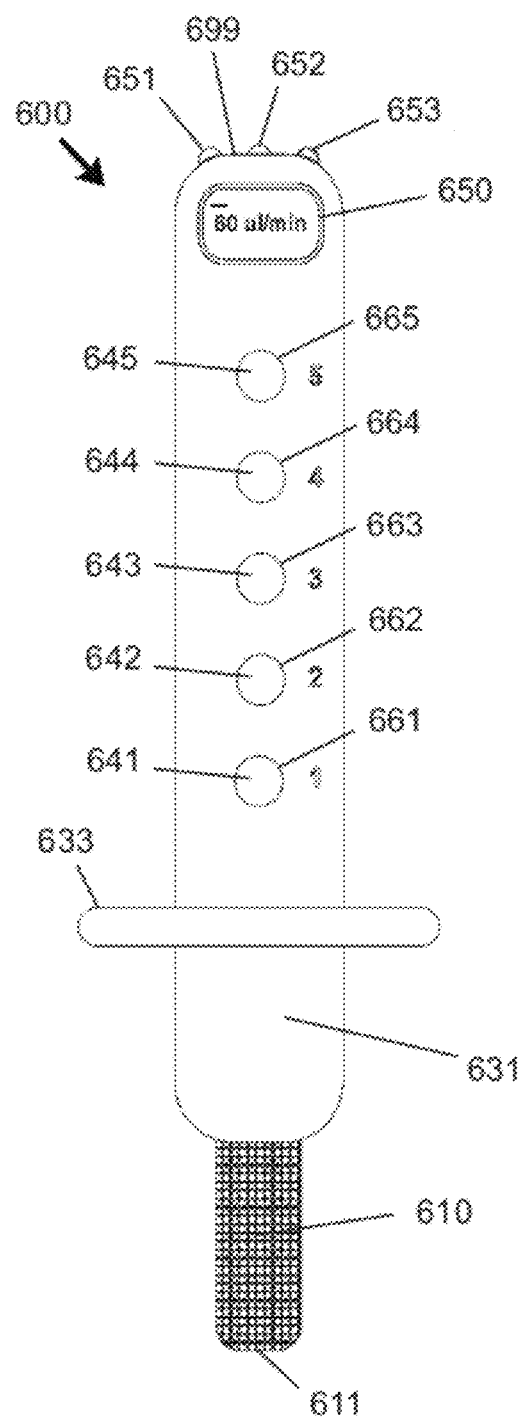
FIG._5  FIG._6

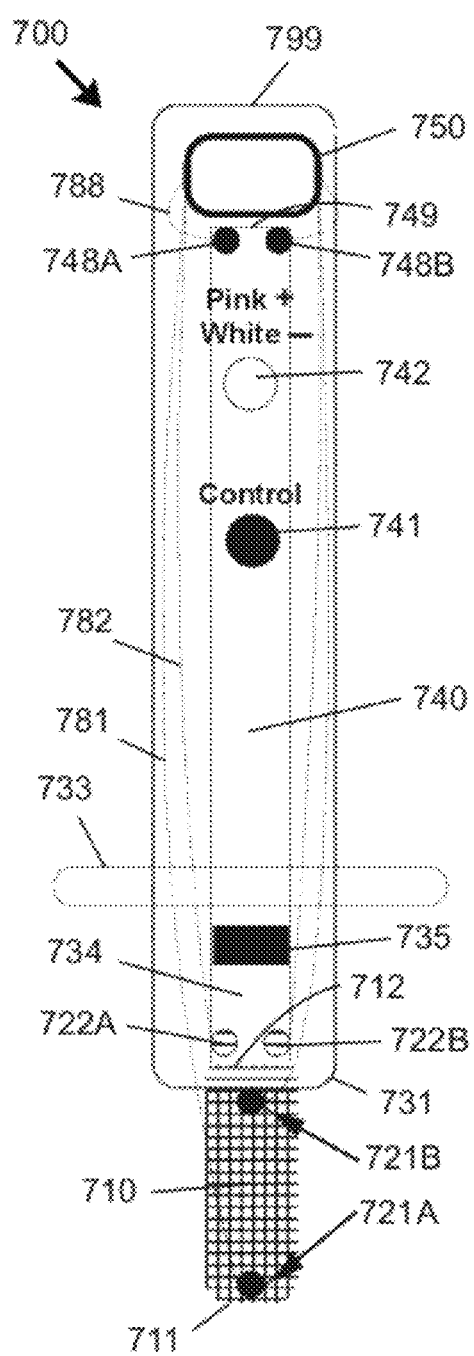
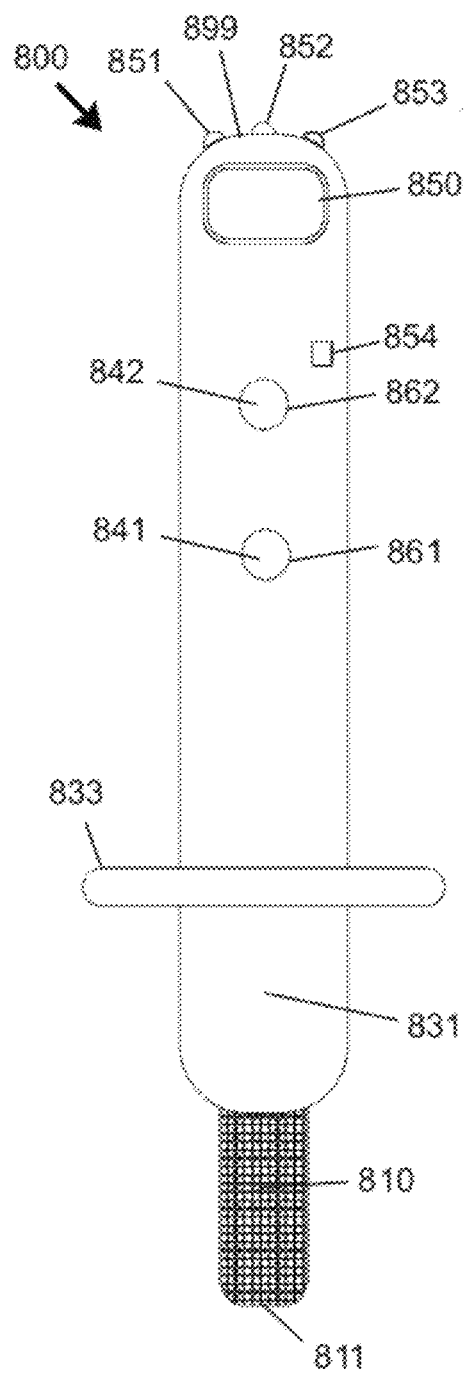
FIG._7   FIG._8

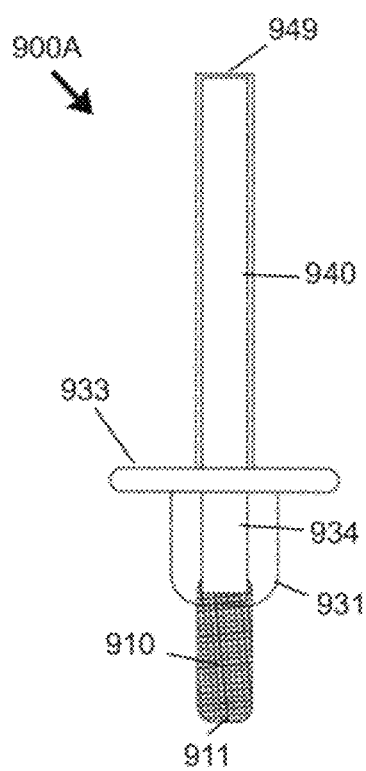
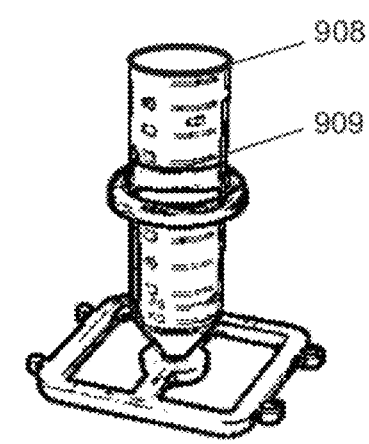
FIG._9A
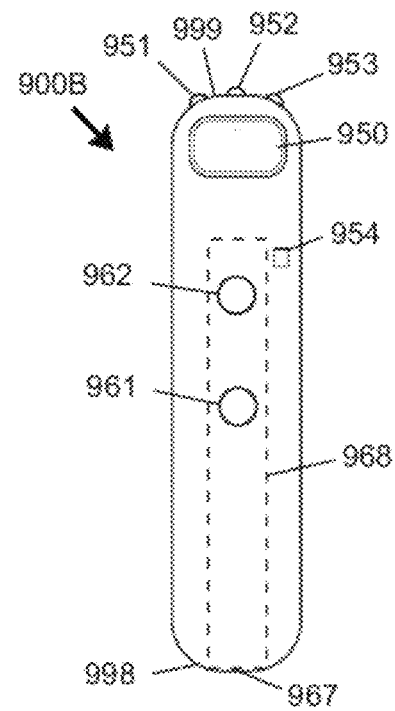
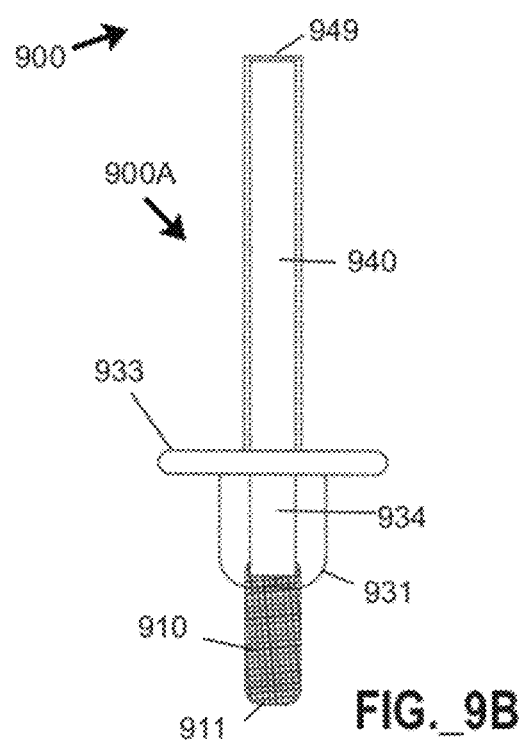
FIG._9B

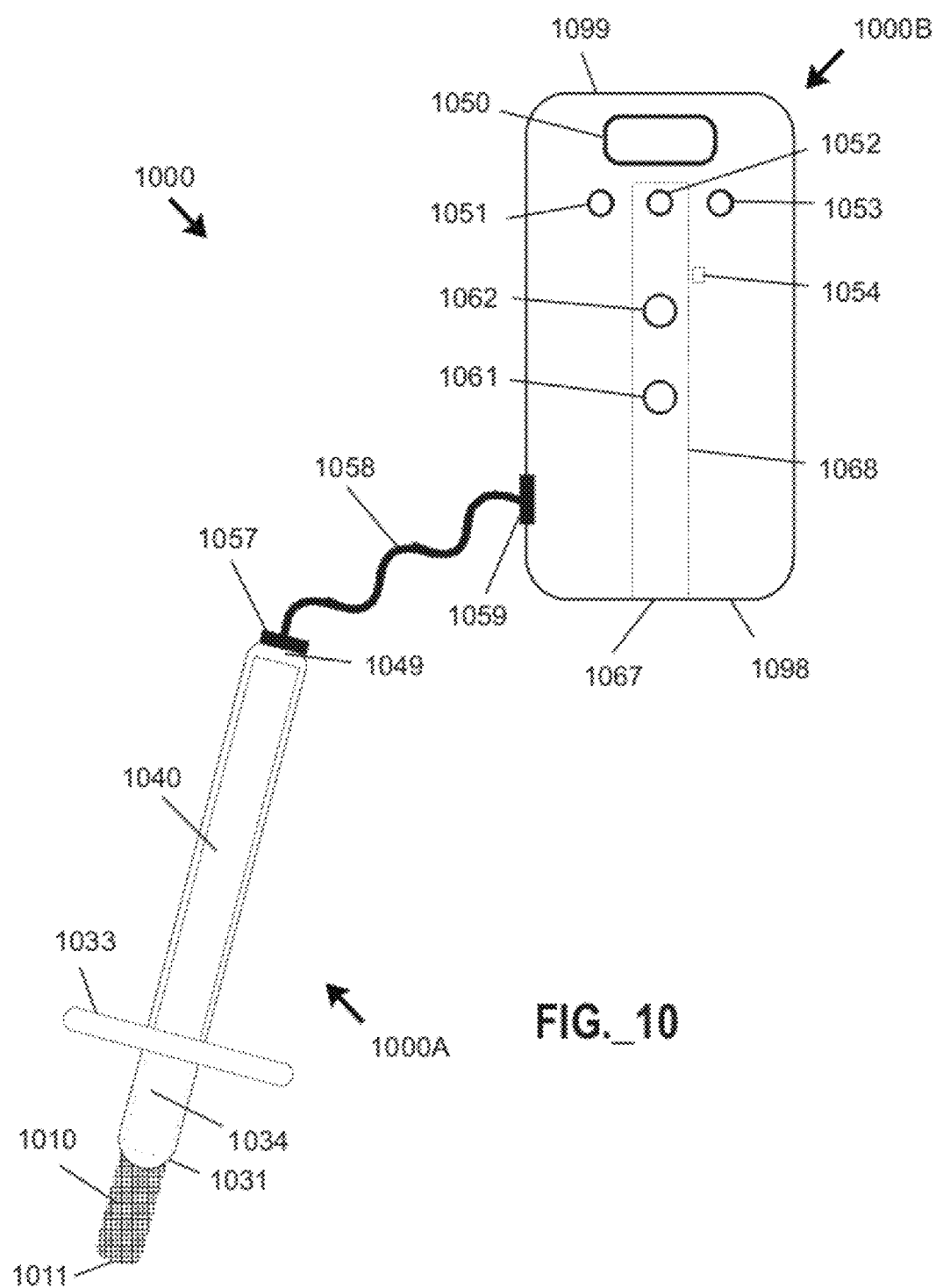
FIG._10

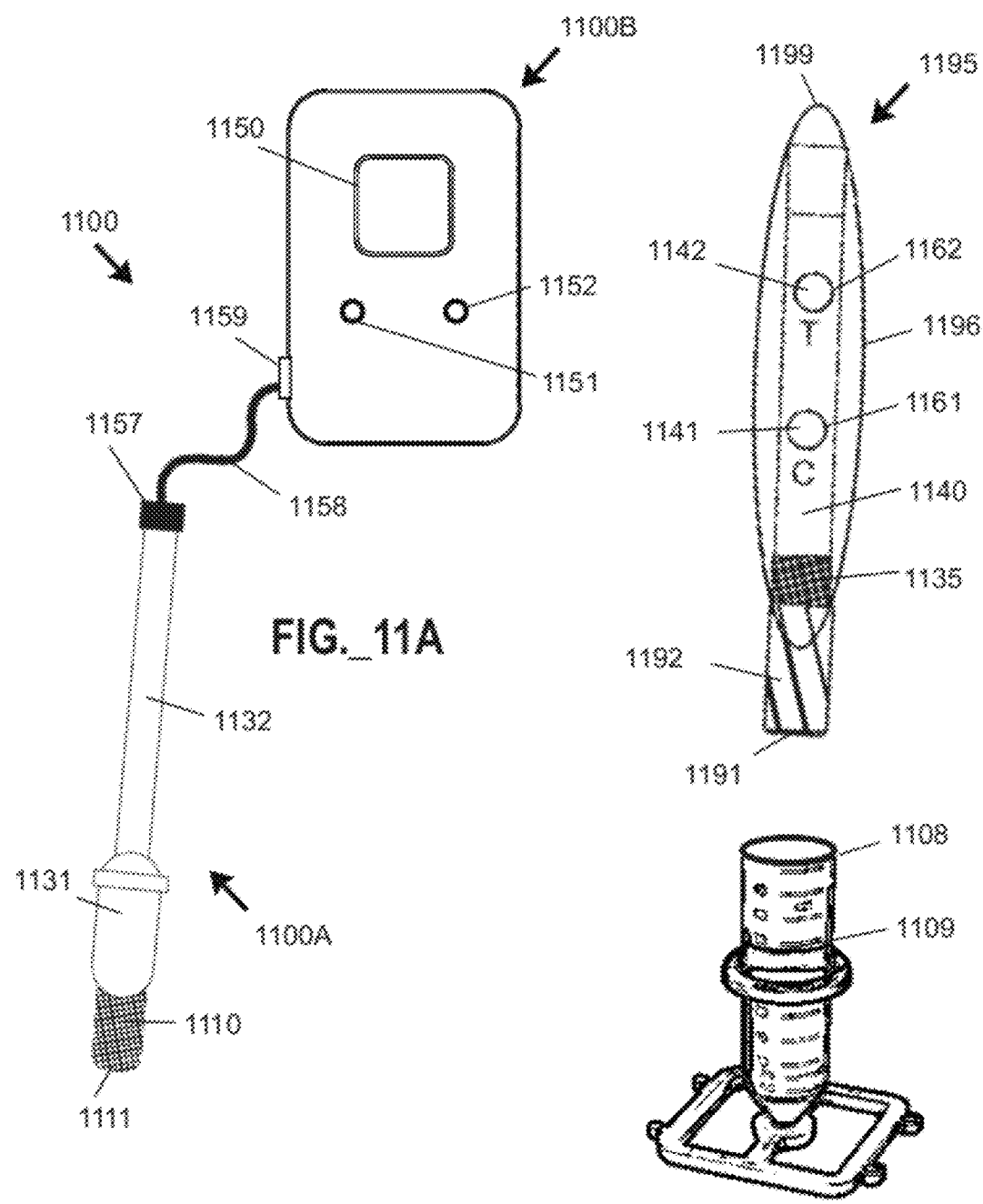

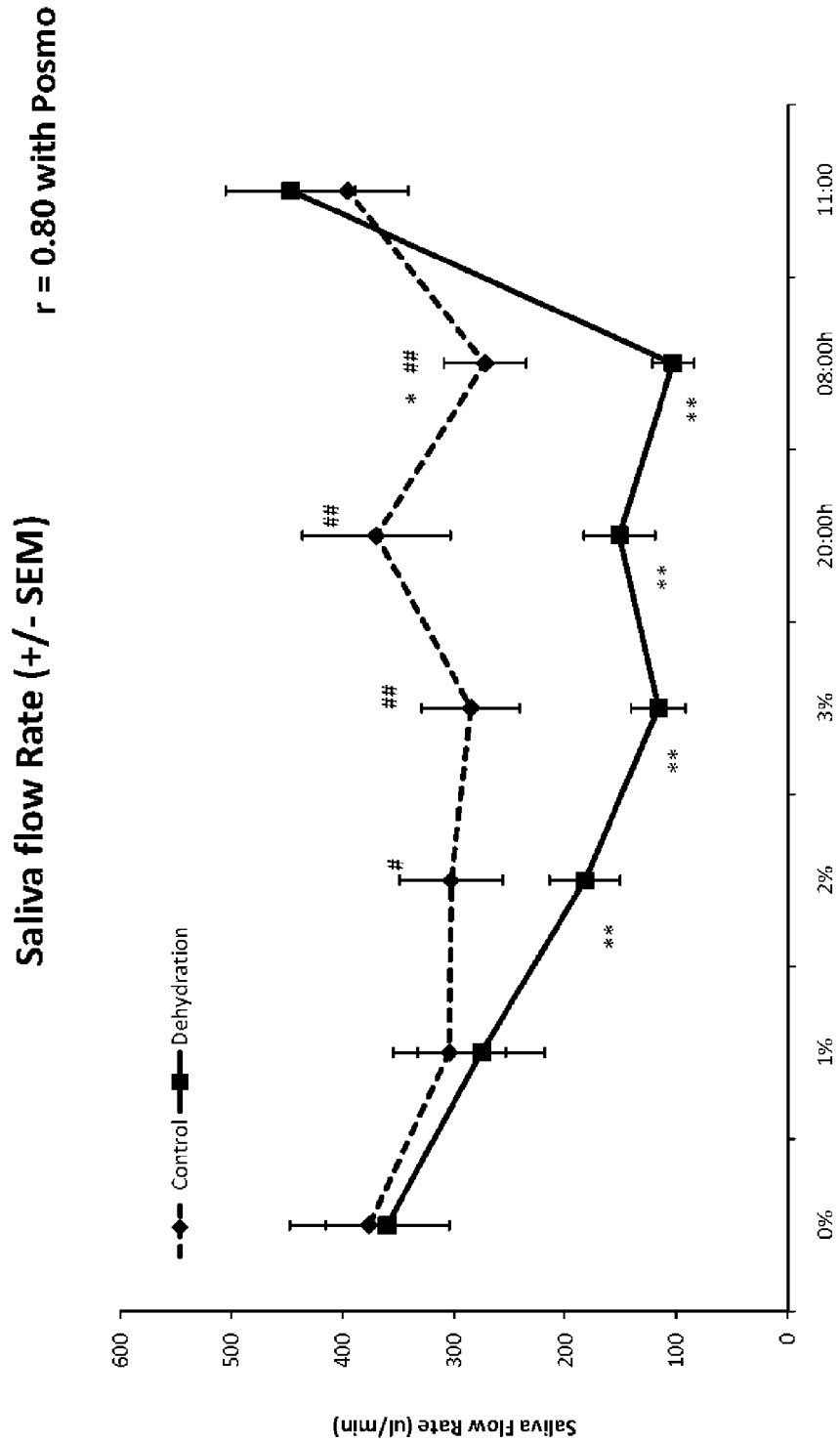
FIG._12

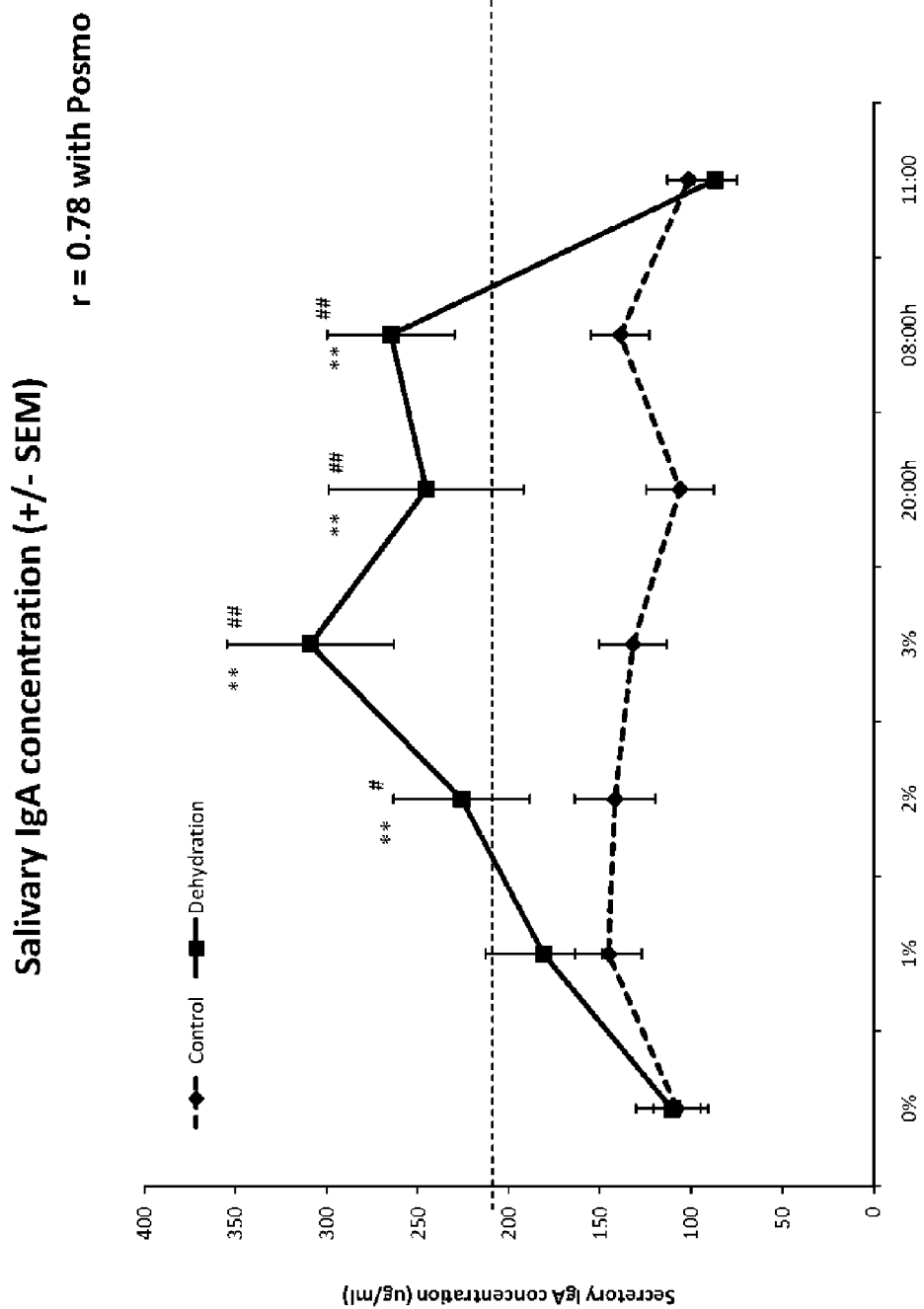
FIG._13

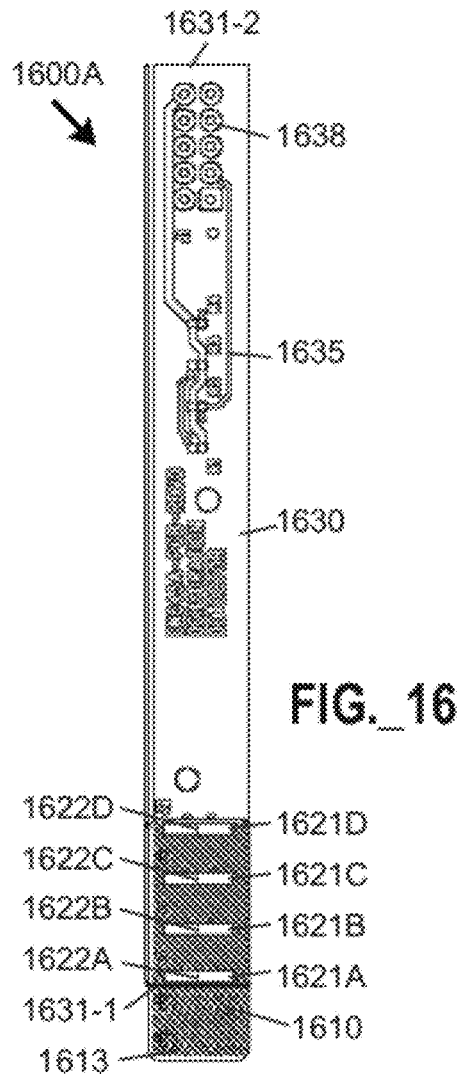
FIG._16
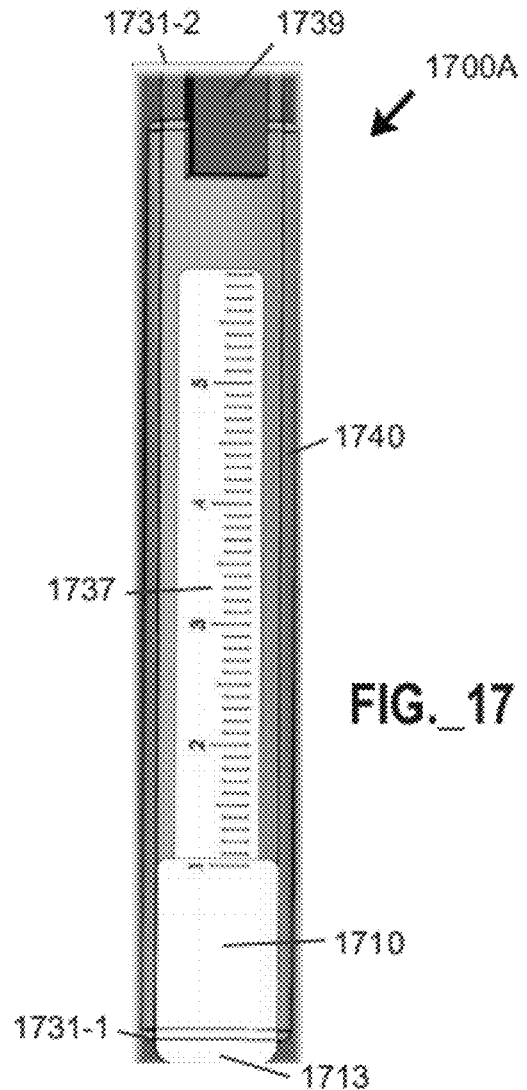
FIG._17
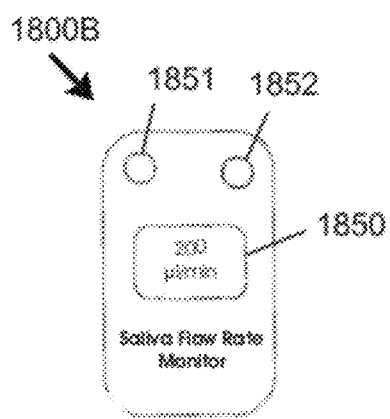
FIG._18
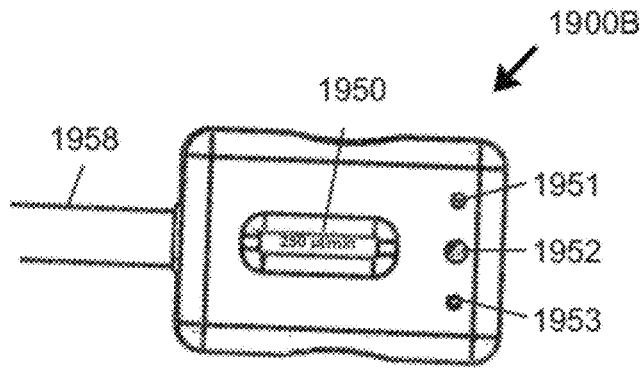
FIG._19

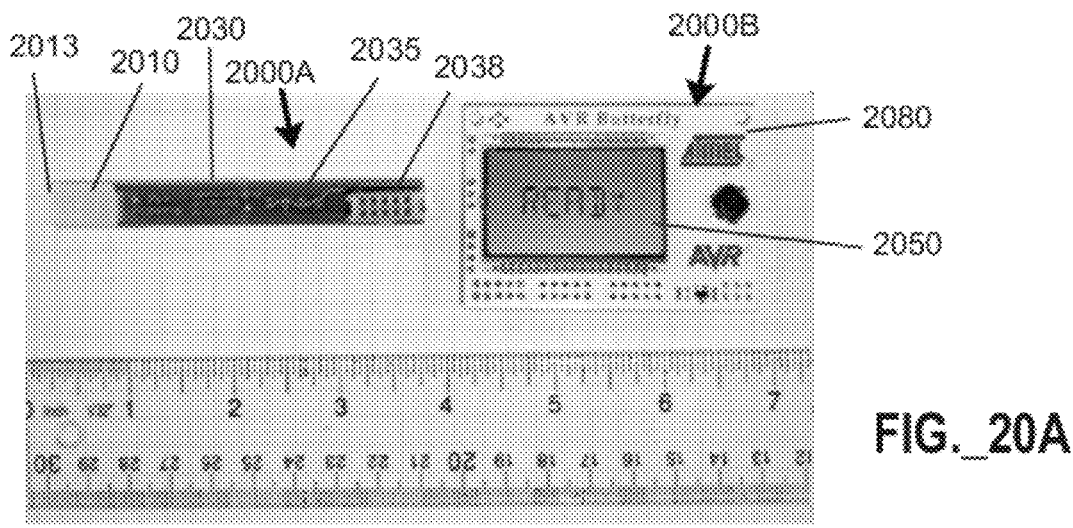
FIG._20A
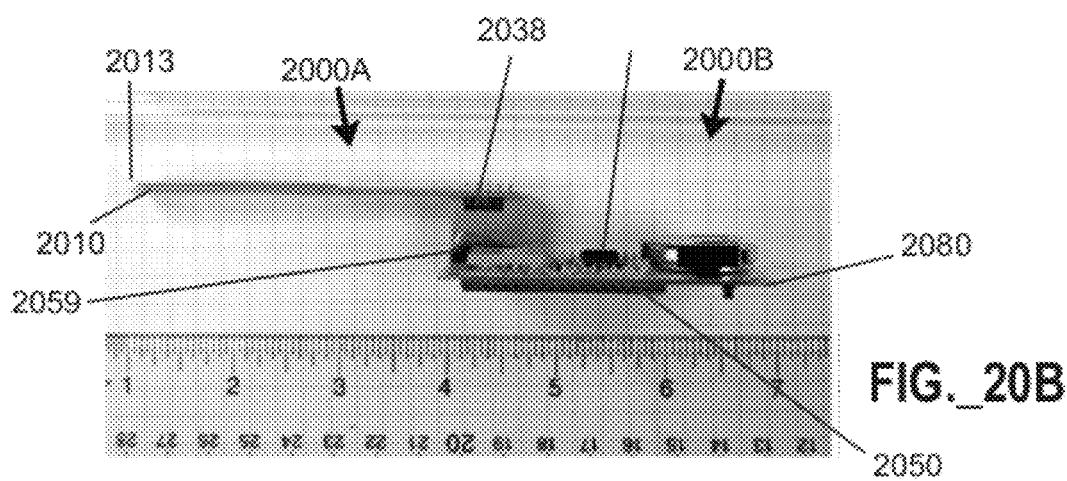
FIG._20B
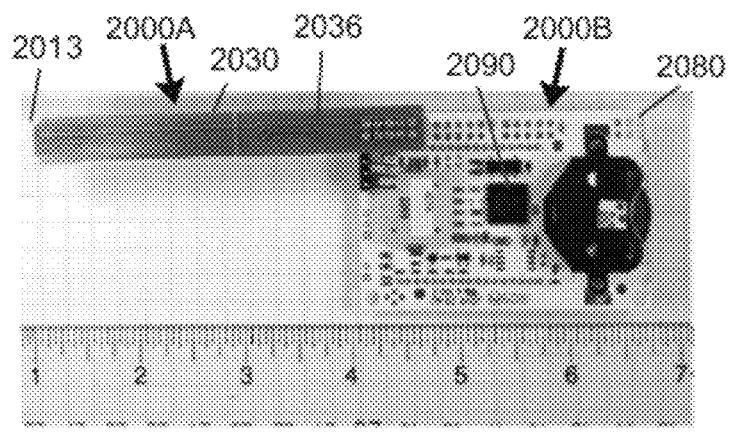
FIG._20C

| Pad in Tube | Time Between Electrodes (sec) | | | | Flow Rate |
|---|---|---|---|---|---|
| X5168 | A - B | A - C | A - D | Vol (ul) | (ul/min) |
| Test 1 | 0.88 | 3.4 | 6.97 | 100 | 861 |
| Test 2 | 0.8 | 3.32 | 7.67 | 98 | 767 |
| Test 3 | 0.45 | 1.57 | 3.67 | 119 | 1946 |
| Test 4 | 0.86 | 2.61 | 5.98 | 104 | 1043 |
| Test 5 | 0.65 | 1.39 | 3.53 | 123 | 2091 |
| Mean | 0.73 | 2.46 | 5.56 | 108.80 | 1341.42 |
| SD | 0.18 | 0.95 | 1.89 | 11.43 | 627.77 |
| %CV | 25 | 39 | 34 | 11 | 47 |

FIG._21A

| Pad in Tube | Time Between Electrodes (sec) | | | | Flow Rate |
|---|---|---|---|---|---|
| D4607 Parallel | A - B | A - C | A - D | Vol (ul) | (ul/min) |
| Test 1 | 0.72 | 2.01 | 4.51 | 181 | 2408 |
| Test 2 | 0.96 | 3.48 | 6.76 | 167 | 1482 |
| Test 3 | 1.54 | 2.4 | 4.96 | 96 | 1161 |
| Test 4 | 0.94 | 2.68 | 4.66 | 145 | 1867 |
| Test 5 | 1.18 | 3.33 | 7.31 | 111 | 911 |
| Mean | 1.07 | 2.78 | 5.64 | 140.00 | 1565.91 |
| SD | 0.31 | 0.62 | 1.30 | 36.10 | 591.45 |
| %CV | 29 | 22 | 23 | 26 | 38 |

FIG._22A

| Pad in Tube | Time Between Electrodes (sec) | | | | Flow Rate |
|---|---|---|---|---|---|
| D4607 Perpend | A - B | A - C | A - D | Vol (ul) | (ul/min) |
| Test 1 | 1.03 | 1.87 | 4.73 | 177 | 2245 |
| Test 2 | 0.9 | 2.47 | 4.78 | 156 | 1958 |
| Test 3 | 0.95 | 2.99 | 5.49 | 154 | 1683 |
| Test 4 | 0.96 | 1.97 | 4.46 | 116 | 1561 |
| Mean | 0.96 | 2.33 | 4.87 | 150.75 | 1861.75 |
| SD | 0.05 | 0.52 | 0.44 | 25.40 | 305 |
| %CV | 6 | 22 | 9 | 17 | 16 |

FIG._23A

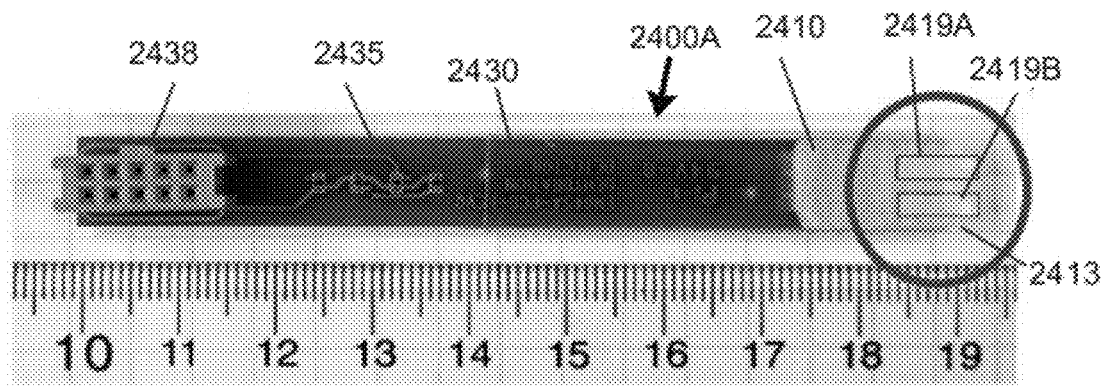
FIG._24A
| Pad in Tube - Yellow Shield | Stimulated Collection* | | | | | | |
|---|---|---|---|---|---|---|---|
| | Time Between Electrodes (sec) | | | | Flow Rate (ul/min) | | |
| D4607 Perpend | A - B | A - C | A - D | Vol (ul) | A - B FR | A - C FR | A - D FR |
| Test 1 | 3.22 | 6.22 | 8.55 | 137.00 | 2553 | 1322 | 961 |
| Test 2 | 5.12 | 7.64 | 10.31 | 128.00 | 1500 | 1005 | 745 |
| Test 3 | 4.43 | 6.98 | 11.72 | 116.00 | 1571 | 997 | 594 |
| Mean | 4.26 | 6.95 | 10.19 | 127.00 | — | — | — |
| SD | 0.96 | 0.71 | 1.59 | 10.54 | — | — | — |
| %CV | 22.59 | 10.23 | 15.58 | 8.30 | — | — | — |
FIG._24B
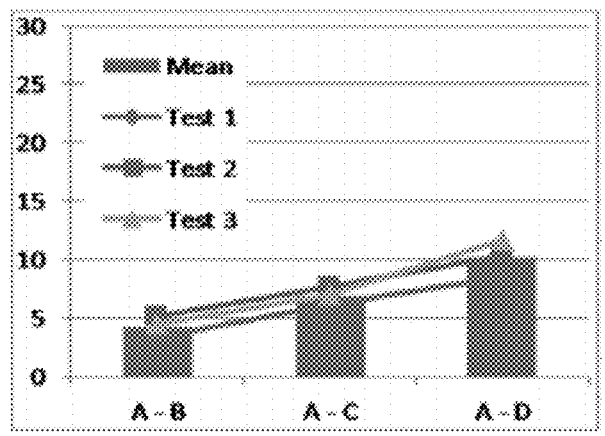
FIG._24C

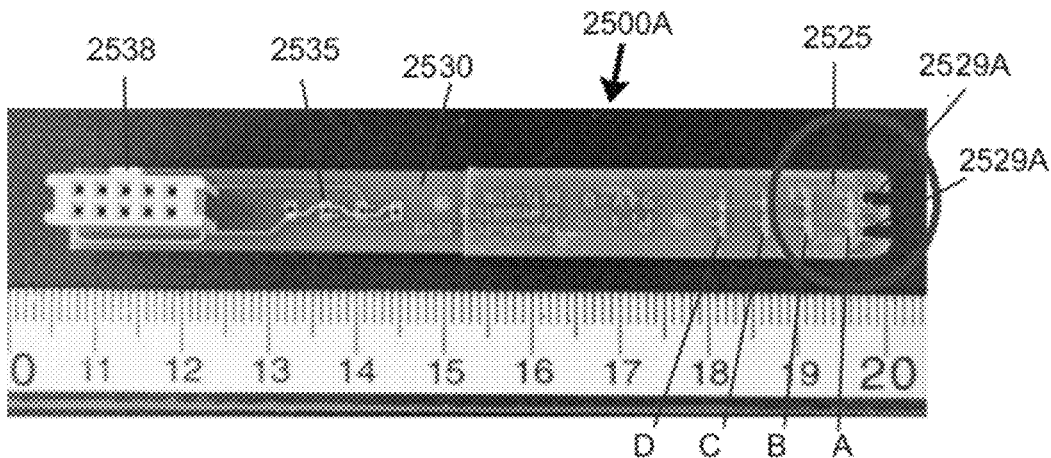
FIG._25A
| Pad in Tube - Clear Shield | Stimulated Collection* | | | | | | |
|---|---|---|---|---|---|---|---|
| | Time Between Electrodes (sec) | | | | Flow Rate (ul/min) | | |
| D4607 Perpend | A - B | A - C | A - D | Vol (ul) | A - B FR | A - C FR | A - D FR |
| Test 1 | 5.66 | 7.94 | 13.83 | 163.00 | 1728 | 1232 | 707 |
| Test 2 | 7.23 | 8.79 | 10.03 | 156.00 | 1295 | 1065 | 933 |
| Test 3 | 5.13 | 10.23 | 11.71 | 131.00 | 1532 | 768 | 671 |
| Mean | 6.01 | 8.99 | 11.86 | 150.00 | — | — | — |
| SD | 1.09 | 1.16 | 1.90 | 16.82 | — | — | — |
| %CV | 18.18 | 12.88 | 16.06 | 11.22 | — | — | — |
FIG._25B
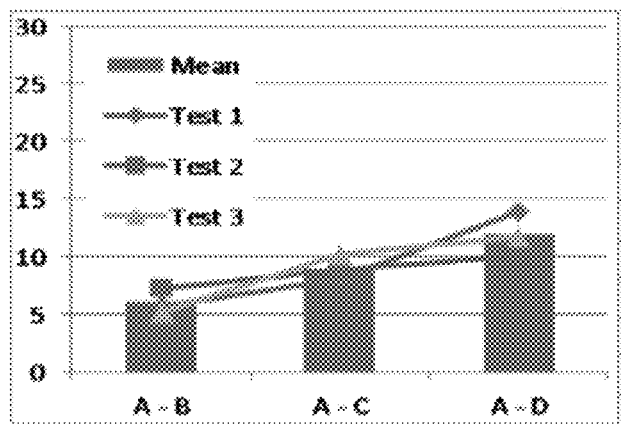
FIG._25C

DIAGNOSTIC DEVICE AND METHOD FOR SENSING HYDRATION STATE OF A MAMMALIAN SUBJECT

STATEMENT OF RELATED APPLICATIONS

This application claims benefit of U.S. Provisional Patent Application No. 61/388,234 filed on Sep. 30, 2010 and U.S. Provisional Patent Application No. 61/450,977 filed on Mar. 9, 2011, and is also a continuation of International Patent Application No. PCT/US11/54104 filed on Sep. 29, 2011. The entire contents of the each foregoing applications are hereby incorporated by reference for all purposes.

FIELD OF THE INVENTION

The present invention relates to sensing of physiological conditions including hydration state (e.g., euhydration or dehydration) utilizing saliva of mammalian subjects.

BACKGROUND

Maintaining appropriate hydration level is critical for health and performance of humans and other mammals. Water lost through processes including perspiration and respiration must be replaced. Fluid losses of between 2-3% of body mass detrimentally affect cardiovascular function, thermal dissipation, and exercise performance. Overhydration can also detrimentally affect exercise performance (e.g., due to electrolyte imbalance) and stress a subject's kidneys. Relying upon thirst as a feedback mechanism to trigger demand for fluid intake may not be adequate to maintain an optimal hydration level, since a sensation of thirst sufficient to cause a subject to drink may not be triggered until after the subject is already dehydrated.

One method to assess hydration is to periodically weigh a subject under controlled conditions. For example, over a bout of exercise, a reduction in body weight measured nude before and after exercise will indicate a state of dehydration. While nude body weight changes may be used to assess acute changes in hydration status during a single exercise bout, over longer periods of time, body weight changes may be influenced by many factors other than change in hydration status, such as: food intake, bowel movements, and changes in body composition. As a result, measurement of body weight over a prolonged period is an inaccurate way of assessing whole body hydration status. But even in a single bout of exercise, it may be highly impractical to stop and subject for purposes of measuring nude body weight to assess hydration status.

Other known methods to assess hydration status involve use of testing of urine or blood. For example, urine specific gravity is a common standard among certain physicians. For patients that can be monitored over time, total urine output or urine specific gravity may be used as a metric. Hydration status can also be assessed using a blood sample, since an increase in plasma osmolality can often identify a state of dehydration, but such sensing requires invasive collection of a venous blood sample by a qualified phlebotomist. In numerous settings, use of urine or blood for assessment of hydration status can be highly impractical.

For many reasons, saliva is an ideal choice for development of a rapid, point-of-care diagnostic measurement for dehydration and/or stress. The sample is easily obtained with minimal invasiveness. No blood must be drawn. In many cases, it is difficult for an individual or health care provider to access urine in a patient (especially for the elderly or infants). Also, urine assessment could be indicative of a prior state of dehydration because the urine is maintained in the bladder and does not necessarily reflect a subject's current hydration state. It would be desirable to provide a convenient device and method for sensing hydration status without requiring use of conventional laboratory equipment and specially trained personnel.

Detection of a constituent in saliva has been proposed for sensing hydration status, such as in U.S. Patent Application Publication No. 2008/0050451 to Mabry ("Mabry"). Mabry discloses an assay device embodied in a test strip including a series of reaction zones with monoclonal antibodies capable of binding salivary amylase in a saliva sample, and reagents for colorimetric detection of the resulting antibodies with bound salivary amylase to provide a visual determination of salivary amylase concentration as a proxy for hydration status. Unfortunately, variations in biomarker level among different samples due to environmental factors, genetic factors, disease state, or other factors, as well as difficulties in obtaining adequate signal to noise ratio to overcome variations in the assay technique, may reduce the ability of such assays to reliably assess hydration status.

Another approach to sensing hydration utilizing saliva involves sensing the viscosity thereof, such as proposed in U.S. Patent Application Publication No. 2007/0048224 to Howell et al. ("Howell et al."). Howell et al. proposes use of a sensing element embodied in a water-permeable material (e.g., blotting paper or cloth) or in a tube, and sensing either the extent or duration of migration of saliva through a portion of the sensing element (since migration rate is affected by salivary viscosity), based on the understanding that viscosity of saliva corresponds to hydration status. Unfortunately, various factors can affect the ability of salivary viscosity to predict hydration status. Such factors include recency of food or beverage consumption or use of chewing gum (as recognized by Howell et al. at ¶[0149]), or occurrence of certain disease status affecting salivary viscosity (as recognized by Howell et al. at ¶[0152]). Although Howell et al. propose the use of an environmental temperature sensor, an environmental humidity sensor, a body temperature sensor, a user location sensor, or a user activity level sensor (e.g., a pedometer) to provide further input regarding the optimal amount of fluid to be consumed by a user, Howell et al. do not disclose any means to overcome potential errors in detecting salivary viscosity as a proxy for user hydration status.

Based on the foregoing, the art continues to seek diagnostic devices and methods for sensing hydration state of a mammalian subject that are adapted to overcome one or more of the foregoing limitations.

SUMMARY OF THE INVENTION

Certain embodiments according to the present invention relate to timed sensing of collection of saliva in a liquid collection element as indicative of state of euhydration, state of dehydration, or salivary secretion rate. In certain embodiments, sensing of salivary flow rate may be further augmented by sensing concentration of at least one analyte in saliva (e.g., with an immunochromatographic assay performed in a lateral flow device) in order to determine a state of euhydration or dehydration. In certain embodiments, production of saliva by a mammalian subject is stimulated, collected, and analyzed to generate an analyte detection signal (e.g., quantitative or qualitative signal) useful for sensing a state of euhydration or dehydration of the subject.

In one aspect, the invention relates to an apparatus for sensing a state of euhydration, state of dehydration, or salivary secretion rate of a mammalian subject, the apparatus comprising: a liquid collection element arranged for placement in fluid communication with oral mucosa of a mammalian subject, the liquid collection element being liquid-permeable, being arranged to transport liquid by wicking, and having a predefined liquid holding capacity; a substrate arranged to support or engage the liquid collection element, with the substrate having arranged thereon a plurality of electrical contact pairs including a first electrical contact pair and a second electrical contact pair arranged downstream of the first electrical contact pair, wherein the first electrical contact pair is arranged to close a first electrical circuit upon exposure to saliva when the liquid collection element is placed in fluid communication with oral mucosa of the mammalian subject, and the second electrical contact pair is arranged to close a second electrical circuit upon exposure to saliva transported though at least a portion of the liquid collection element; a timing element arranged to receive a signal indicative of closure of the first electrical circuit, arranged to receive a signal indicative of closure of the second electrical circuit, and arranged to generate a first time value indicative of time elapsed between the closure of the second electrical circuit and the closure of the first electrical circuit; and a signaling element arranged to generate an output signal indicative of state of euhydration, state of dehydration, or salivary secretion rate of the mammalian subject based at least in part on the first time value.

In another aspect, the invention relates to an apparatus for sensing a state of euhydration, state of dehydration, or salivary secretion rate of a mammalian subject, the apparatus comprising: a liquid collection element arranged for placement in fluid communication with oral mucosa in the mouth of a mammalian subject, the liquid collection element being liquid permeable, being arranged to transport liquid by wicking, and having a predefined liquid holding capacity; a salivary stimulating agent arranged for placement into the mouth of the mammalian subject prior to or substantially concurrently with placement of the at least a portion of the liquid collection element in fluid communication with oral mucosa of the mammalian subject; at least one first electrode or sensing element arranged to sense a condition indicative of exposure of a portion of the liquid collection element to oral mucosa in the mouth of a mammalian subject; at least one second electrode or sensing element arranged to sense a condition indicative of movement by saliva through at least a portion of the liquid collection element; a timing element arranged to be initiated responsive to receipt of a signal from or detection of change of state of the at least one first electrode or sensing element, and to generate a time value indicative of elapsed time since said initiation upon receipt of a signal from or detection of a change of state of the at least one second electrode or sensing element; and a signaling element arranged to generate an output signal indicative of state of euhydration, state of dehydration, or salivary secretion rate of the mammalian subject based at least in part on the time value.

Further aspects of the invention relate to methods utilizing the foregoing apparatuses for sensing a state of euhydration, state of dehydration, or salivary secretion rate of a mammalian subject.

A further aspect of the invention relates to method of sensing a state of euhydration, state of dehydration, or salivary secretion rate of a mammalian subject, the method comprising: inserting a salivary stimulating agent into the mouth of the mammalian subject to stimulate saliva flow; placing at least a portion of a liquid collection element of predefined liquid holding volumetric capacity in contact with oral mucosa of the mammalian subject; detecting a condition indicative of presence of saliva on or adjacent to the liquid collection element upon exposure of the at least a portion of the liquid collection element to oral mucosa of the mammalian subject, and responsively starting a timer; detecting a condition indicative of movement of saliva through at least a portion of the liquid collection element while the at least a portion of the liquid collection element is exposed to oral mucosa of the mammalian subject, and responsively storing a time value indicative of elapsed time since the timer was started; and utilizing the time value to generate an output signal indicative of state of euhydration, state of dehydration, or salivary secretion rate of the mammalian subject.

Still another aspect of the invention relates to a method for sensing a state of euhydration or dehydration of a mammalian subject, the method comprising: placing at least a portion of a liquid collection element of predefined liquid holding volumetric capacity in contact with oral mucosa of the mammalian subject; detecting presence of saliva at first, second, and third positions along or adjacent to the liquid collection element with respect to time while the at least a portion of the liquid collection element is in contact with oral mucosa of the mammalian subject, to determine a first time value indicative of migration of saliva from the first position to the second position, and to determine a second time value indicative of migration of saliva between the second position and the third position; and utilizing the first time value and the second time value to generate an output signal indicative of state of euhydration, state of dehydration, or salivary secretion rate of the mammalian subject. Certain embodiments may further include detecting presence of saliva at a fourth position along or adjacent to the liquid collection element, to determine a third time value indicative of migration of saliva between the third position and the fourth position.

In another aspect, the invention relates to a method for sensing a state of euhydration or dehydration of a mammalian subject, the method comprising: sensing a condition indicative of rate of migration of saliva through at least a portion of a liquid collection element in fluid communication with oral mucosa in the mouth of a mammalian subject utilizing at least one sensor in sensory communication with the liquid collection element, and generating a first signal correlative of the sensed condition; sensing concentration of at least one analyte in saliva received from the mammalian subject, the analyte being selected from the group consisting of secretory IgA, albumin, secretory component, and aldosterone, and generating a second signal correlative of concentration of the at least one analyte; and utilizing the first signal and the second signal to generate an output signal indicative of state of euhydration, state of dehydration, or salivary secretion rate of the mammalian subject.

Further aspects of the invention relate to use of the described devices and methods to diagnose a disease state of the mammalian subject, and/or to detect a side effect of drug interaction with the mammalian subject In a further aspect, any of the foregoing aspects or features and elements as disclosed herein may be combined for additional advantage.

Other aspects, features and embodiments of the invention will be more fully apparent from the ensuing disclosure and appended claims.

BRIEF DESCRIPTION OF THE DRAWINGS

FIG. 1 is a schematic diagram showing interconnection of various components of a system for sensing a state of euhydration or dehydration of a mammalian subject via saliva of the subject according to one embodiment of the present invention.

FIG. 2 is a side cross-sectional schematic view of a portion of a saliva collection element arranged in contact with a saliva collection interface device having integral electrodes for use with systems and methods according to certain embodiments of the present invention.

FIG. 3 is a side cross-sectional schematic view of a saliva collection element having integral electrodes, a backing element, and a covering element for use with systems and methods according to certain embodiments of the present invention.

FIG. 4 is top plan schematic view of a saliva collection element having integral electrodes with a guide channel portion arranged between two electrode pairs for use with systems and methods according to certain embodiments of the present invention.

FIG. 5 is a top cross-sectional schematic view of a first apparatus for sensing a state of euhydration or dehydration of a mammalian subject via saliva of the subject according to one embodiment of the present invention, with the apparatus arranged to sense both salivary secretion rate and concentration of at least one analyte in saliva, to provide a quantitative output signal based on salivary secretion rate, and to provide a qualitative signal based on analyte concentration.

FIG. 6 is a top plan schematic view of a second apparatus (similar to the apparatus of FIG. 5) for sensing a state of euhydration or dehydration of a mammalian subject via saliva of the subject according to one embodiment of the present invention, with the apparatus arranged to sense both salivary secretion rate and concentration of at least one analyte in saliva, to provide a quantitative output signal based on salivary secretion rate, and to provide a qualitative signal based on analyte concentration.

FIG. 7 is a top cross-sectional schematic view of a third apparatus for sensing a state of euhydration or dehydration of a mammalian subject via saliva of the subject according to one embodiment of the present invention, with the apparatus arranged to sense both salivary secretion rate and concentration of at least one analyte in saliva, to provide a qualitative output signal based on salivary secretion rate, and to provide a qualitative signal based on analyte concentration.

FIG. 8 is a top plan schematic view of a fourth apparatus (similar to the apparatus of FIG. 7) for sensing a state of euhydration or dehydration of a mammalian subject via saliva of the subject according to one embodiment of the present invention, with the apparatus arranged to sense both salivary secretion rate and concentration of at least one analyte in saliva, to provide a qualitative output signal based on salivary secretion rate, and to provide a qualitative signal based on analyte concentration.

FIG. 9A illustrates a sampling portion of an apparatus for sensing a state of euhydration or dehydration of a mammalian subject via saliva of the subject according to one embodiment of the present invention, arranged proximate to a vial of buffer solution prior to contacting of a portion of the sampling portion with the buffer solution.

FIG. 9B illustrates the sampling portion of FIG. 9A arranged proximate to a monitoring portion of the apparatus for sensing a state of euhydration or dehydration of a mammalian subject via saliva of the subject according to one embodiment of the present invention, prior to insertion of a portion of the sampling portion into the monitoring portion.

FIG. 10 illustrates a sampling portion and a monitoring portion of an apparatus for sensing a state of euhydration or dehydration of a mammalian subject via saliva of the subject according to one embodiment of the present invention, with the monitoring portion connected via an electrical communication cable to the sampling portion.

FIG. 11A illustrates a salivary secretion rate sensing apparatus of a system for sensing a state of euhydration or dehydration of a mammalian subject via saliva of the subject according to one embodiment of the present invention.

FIG. 11B illustrates a salivary analyte concentration sensing apparatus of a system for sensing a state of euhydration or dehydration of a mammalian subject via saliva of the subject according to one embodiment of the present invention, with a liquid collection element thereof arranged proximate to a vial of buffer solution.

FIG. 12 is a line chart embodying values of salivary flow rate (ml/min) plotted as a function of time for a first control group of research study participants, and values of salivary flow rate (ml/min) plotted as a function of percentage body mass loss and time for a second dehydration group of research study participants, showing that dehydration is accompanied by a reduction in salivary flow rate (i.e., secretion rate).

FIG. 13 is a line chart embodying values of secretory IgA concentration ($\mu$g/ml) plotted as a function of time for a first control group of research study participants, and values of salivary flow rate (ml/min) plotted as a function of percentage body mass loss and time for a second dehydration group of research study participants, showing that dehydration is accompanied by an increase in secretory IgA concentration.

FIG. 16 is a top plan view of a sampling portion of an apparatus for sensing hydration state or salivary secretion rate of a mammalian subject, the sampling portion including a liquid collection element arranged over a portion of a circuit board substrate having four sequentially arranged electrical contact pairs for sensing presence of saliva.

FIG. 17 is a top plan view of a sampling portion of another apparatus for sensing hydration state or salivary secretion rate of a mammalian subject, the sampling portion including a liquid collection element supported on or in a substrate having a numeric scale and having a socket arranged for interfacing with a separate monitoring portion (not shown).

FIG. 18 is a top schematic view of a monitoring portion of an apparatus for sensing hydration state or salivary secretion rate of a mammalian subject, the monitoring portion including an alphanumeric display and other user-perceptible indicators and being intended for use with a sampling portion such as described in connection with FIG. 16 or 17.

FIG. 19 is a top schematic view of a monitoring portion of another apparatus for sensing hydration state or salivary secretion rate of a mammalian subject, the monitoring portion including an alphanumeric display, other user-perceptible indicators, and an interface cable, and being intended for use with a sampling portion such as described in connection with FIG. 16 or 17.

FIG. 20A is a top plan view of a sampling portion and a monitoring portion of an apparatus for sensing hydration state or salivary secretion rate of a mammalian subject, with the sampling portion and the monitoring portion being separated from one another.

FIG. 20B is a side elevation view of the apparatus illustrated in FIG. 20A, with the sampling portion connected to the monitoring portion.

FIG. 20C is a bottom plan view of the apparatus illustrated in FIG. 20B, with the sampling portion connected to the monitoring portion.

FIG. 21A is a table summarizing results of five salivary secretion rate sensing tests utilizing a sampling portion with a X5169 collection pad and four sequentially arranged electrical contact pairs A to D.

FIG. 22A is a table summarizing results of five salivary secretion rate sensing tests utilizing a sampling portion with a D4607 parallel collection pad and four sequentially arranged electrical contact pairs A to D.

FIG. 23A is a table summarizing results of four salivary secretion rate sensing tests utilizing a sampling portion with a D4607 perpendicular collection pad and four sequentially arranged electrical contact pairs A to D.

FIG. 24A is a top plan view of a sampling portion of an apparatus for sensing hydration state or salivary secretion rate of a mammalian subject similar to the sampling portion illustrated in FIGS. 20A-20C, but with addition of two colored polymeric strips or loops as shielding elements over portions of the liquid collection element in the form of a D4607 perpendicular collection pad, with the liquid collection element arranged over four sequentially arranged electrical contact pairs A to D.

FIG. 24B is a table providing results of three in vivo stimulated salivary secretion rate sensing tests utilizing the sampling portion of FIG. 24A.

FIG. 24C is a line chart representing time for migration of saliva between respective electrodes of the salivary secretion rate sensing tests summarized in FIG. 24B, superimposed over a bar chart representing average migration times.

FIG. 25A is a top plan view of a sampling portion of an apparatus for sensing hydration state or salivary secretion rate of a mammalian subject similar to the sampling portion illustrated in FIGS. 20A-20C, but with addition of an notch- or aperture-defining clear polymeric shielding element over portions of the liquid collection element in the form of a D4607 perpendicular collection pad, with the liquid collection element arranged over four sequentially arranged electrical contact pairs A to D.

FIG. 25B is a table providing results of three in vivo stimulated salivary secretion rate sensing tests utilizing the sampling portion of FIG. 25A.

FIG. 25C is a line chart representing time for migration of saliva between respective electrodes of the salivary secretion rate sensing tests summarized in FIG. 25B, superimposed over a bar chart representing average migration times

DETAILED DESCRIPTION

The present invention relates in various embodiments to sensing of salivary secretion rate (e.g., as may be measured by sensing time to collection of saliva in multiple portions or the entirety of a liquid collection) as indicative of state of euhydration or dehydration. As noted previously, determination of state of euhydration or dehydration may be further aided by sensing of at least one analyte in saliva.

Figure 14:
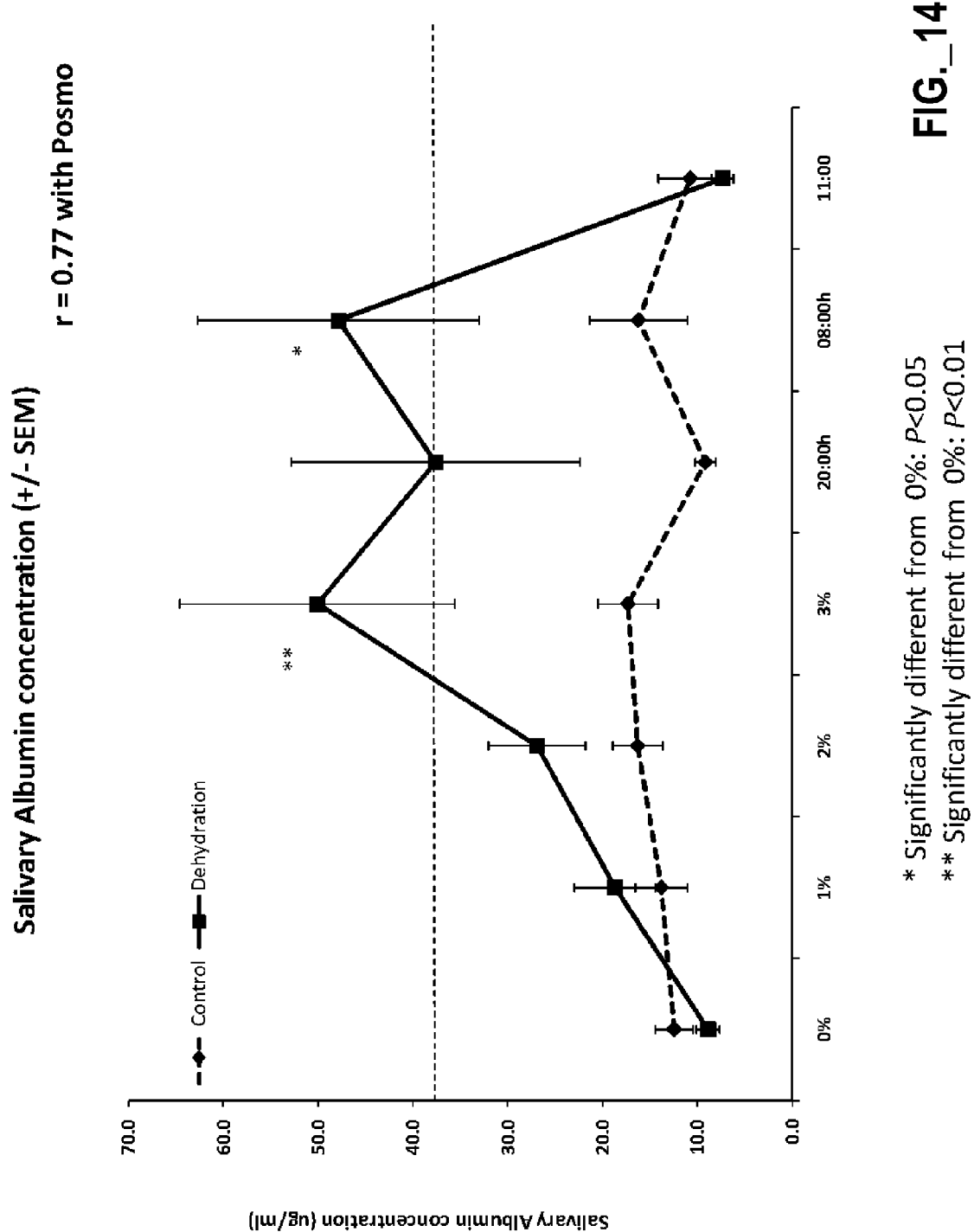
FIG. 14 is a line chart embodying values of salivary albumin concentration ($\mu$g/ml) plotted as a function of time for a first control group of research study participants, and values of salivary flow rate (ml/min) plotted as a function of percentage body mass loss and time for a second dehydration group of research study participants, showing that dehydration is accompanied by an increase in salivary albumin concentration.
Figure 15:
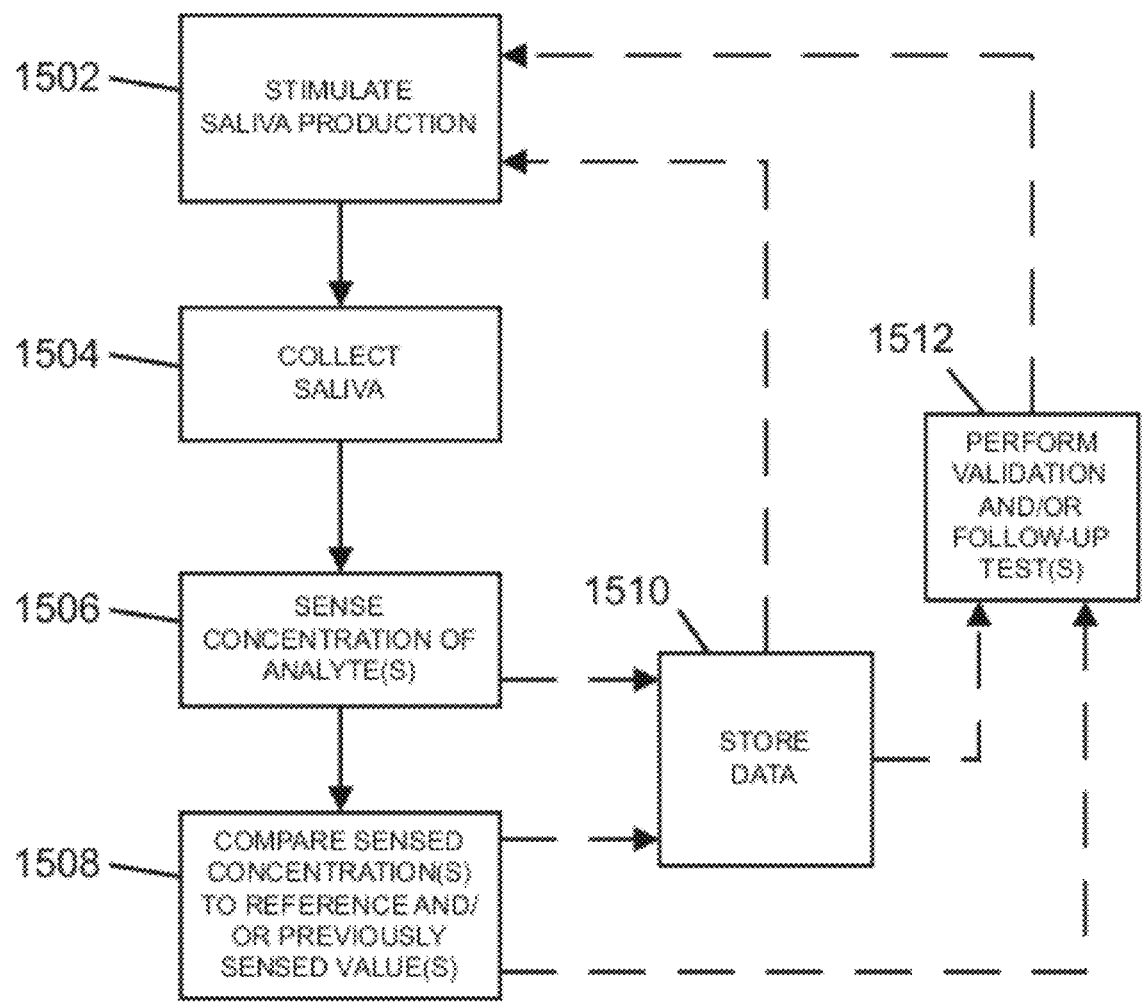
FIG. 15 is a flowchart illustrating various steps of a method for sensing a state of euhydration or dehydration of a mammalian subject including stimulating production of saliva of the subject and sensing of concentration of one or more analytes in the saliva, according to one embodiment of the present invention.

Research recently performed by Dr. Neil P. Walsh of the University of Wales (Bangor) School of Sport, Health and Exercise Sciences (as subsidized by the assignee of the present application and not yet published) has demonstrated that dehydration is accompanied by a reduction in salivary secretion rate, as well as increases in certain analyte contained in saliva, such as IgA and albumin. FIGS. 13-15 embody line charts including values of salivary flow rate, secretory IgA concentration, and salivary albumin concentration, respectively, plotted as a function of time for a first control group of research study participants, and plotted as a function of percentage body mass loss and time for a second dehydration group of research study participants. Although not verified in the above-mentioned study, Applicants have also theorized that dehydration may be accompanied by an increase in salivary aldosterone concentration may be correlative of dehydration.

In certain embodiments, salivary secretion rate may be measured by placing a liquid collection element of predefined liquid holding volumetric capacity in a user's mouth, measuring the time required to saturate the predefined liquid holding capacity of the liquid collection element, and then dividing the predefined volumetric capacity by the resulting time value (e.g., to yield volume divided by time). Such secretion rate may be used to determine state of euhydration, state of dehydration, state of disease (e.g., where the disease state includes hyposalivation as a symptom thereof), and/or to detect a side effect of drug interaction with the mammalian subject. For example, Sjögren's syndrome is a chronic autoimmune disease in which a person's white blood cells attack the person's moisture-producing glands, and such disease is characterized by hyposalivation. Detection of salivary secretion rate below a predetermined threshold (such as may be optionally validated by multiple runs of substantially the same type or multiple tests of different types) utilizing devices and/or methods as disclosed herein may be used to diagnose Sjögren's syndrome. Other disease states may be detected. Similarly, certain drugs are characterized by hyposalivation as a side effect, and devices and/or methods as disclosed herein may be used to detect a side effect of drug interaction with a user (e.g., by comparison of an output signal or an apparatus disclosed herein, or information derived from such signal, with at least one reference value or reference value range correlative of the side effect of drug interaction). In certain embodiments, dosage and/or administration of a drug may be adjusted in response to the detection of a side effect (such as hyposalivation) of the drug interaction. In certain embodiments, an apparatus and/or method as disclosed herein may be used to determine suitability or readiness of a patient to undergo a medical or dental procedure that requires or is benefited by maintenance of a particular saliva secretion rate range or threshold (whether low or high).

In certain embodiments, a process of measuring salivary secretion rate may be automated through use of a timing element that is activated using at least one first electrode or sensing element arranged to sense a condition indicative of exposure of a portion of the liquid collection element to oral mucosa (e.g., under the tongue) in a user's mouth, and that is deactivated using at least one second electrode or sensing element arranged to sense a condition indicative of saturation of the predefined liquid holding capacity while the liquid collection element is exposed to oral mucosa in the user's mouth. A time value indicative of elapsed time since the timer was started may be stored in a memory, and such time value (or a value derived therefrom) may be utilized (at least in part) to generate an output signal indicative of state of euhydration, state of dehydration, or salivary secretion rate of the user.

In certain embodiments, electrodes and/or sensing elements may be arranged in sensory communication with one or more portions of a liquid collection element, with a suitable interface (e.g., via electrically conductive traces, wires, or the like) to processing or control elements arranged to receive signals therefrom. In certain embodiments, such electrodes and/or sensing elements may be deposited on a thin film (e.g., polymeric thin-film) to which a porous or fibrous medium is adhered or otherwise retained. In certain embodiments, complementary electrode pairs each define open circuits that are arranged to be closed by conduction of electric current through saliva in contact therewith. Electrical conductivity of saliva may be enhanced by presence of one or more electrolytes (e.g., sodium chloride) in or on to the liquid collection element arranged to contact saliva. Various types of sensing elements that may be used include capacitive sensing elements, conductivity sensing elements, optical sensing elements, and the like.

Multiple electrodes and/or sensing elements may be arranged in series, in parallel, or in series and parallel configurations. When multiple electrodes and/or sensing elements are used, multiple time values indicative of migration of saliva to predetermined distances and/or to occupy predefined volumes may be established. The multiple values may be processed and/or compared (e.g., using a processing element and/or comparator). Multiple time values may be compared or otherwise processed (e.g., to establish a mean value, deviation from a mean value, difference, ratio, etc.), and one or more resulting values may be used at least in part to establish an output signal.

Since salivary secretion rate, viscosity of produced saliva, and/or mucin interaction may not be uniform during the entire saliva sample collection period, time values indicative of migration of saliva to predetermined distances and/or to occupy predefined volumes may not be equal for migration of saliva from one sensing region (e.g., circuit closure region) to the next, even when multiple sensing regions are equidistantly spaced. In certain embodiments, three, four, or more sensing regions are arranged in series, time values indicative of migration of saliva between different sensing regions are stored (e.g., to establish first and second, or first, second and third (or additional) time values, and an output signal (e.g., indicative of state of euhydration, state of dehydration, or salivary secretion rate) is based on at least in part on the multiple values, on a comparison between two or more time values, and/or at least one processed value derived from the multiple time values.

In certain embodiments, sensing elements are provided in the form of paired electrically conductive traces or contacts each having a gap between two contacts, with the contacts arranged to close an electric circuit upon contact with saliva. Such sensing elements are preferably arranged on a substrate arranged to support or engage a liquid-permeable liquid collection element. Multiple contact pairs may be arranged in series, such that an advancing front of saliva migrating through a liquid collection element may close a first circuit upon closing the gap between a first contact pair, then close a second circuit upon closing the gap between a second contact pair, and thereafter similarly close circuits between respective additional (e.g., third, fourth, etc.) contact pairs, with the closure of each circuit being used to affect operation of at least one timer (or multiple timers) to identify migration time of saliva through one portion, multiple portions, or the entirety of the collection element.

In certain embodiments, an apparatus as described herein may include an electrolyte (e.g., arrangeable in, on, or against a portion of a liquid collection element) to increase conductivity of saliva collected by the liquid collection element.

In certain embodiments, a liquid collection element comprises a porous medium or a fibrous medium arranged to absorb saliva. A liquid collection element may be formed of paper, fabric, nitrocellulose, or any other suitable material. Desired dimensions may be 7×21 mm or 10×15 mm, so as to provide a collection volume in a range of 100 to 150 microliters. In certain embodiments, a liquid collection element comprises a lateral flow test strip. In certain embodiments, a liquid collection element comprises a material having directionally uniform liquid wicking characteristics. In other embodiments, a liquid collection element comprises a material arranged to wick liquid in one direction preferentially relative to another direction. In various embodiments, a liquid collection element includes a wicking element with a preferential flow direction arranged in substantially same direction of intended migration of saliva through the collection element.

In embodiments with a liquid collection element having a preferential flow direction, first and second electrode or sensing elements may be separated along a direction through which liquid does not preferentially wick through a liquid collection element, in order to reduce the possibility that a frontal edge of saliva advancing within a liquid collection element may reach a second electrode or sensing element before the liquid collection element is saturated. A liquid collection element may further utilize selective placement and/or patterning of hydrophobic and/or hydrophilic materials in order to guide a frontal edge of saliva advancing therein in order to promote saturation of a liquid collection element before at least one second electrode or sensing element generates a signal indicating such saturated condition has been attained.

In certain embodiments, a liquid collection element comprises a liquid-permeable porous medium or fibrous medium that is supported by or otherwise engaged with a substrate. In certain embodiments, a substrate may be arranged in contact with one or multiple surfaces of a liquid collection element. In certain embodiments, a substrate may be provided as part of a housing or tube (e.g., formable by injection molding, heat shrink tubing, or another method) that surrounds a portion of a liquid collection element, with another portion of the liquid collection element being exposed. In certain embodiments, a liquid collection element includes a portion of a porous or fibrous material that is sandwiched between liquid-impermeable materials (e.g., polymeric films), with another portion of the liquid collection element having at least one exposed surface arranged to absorb saliva upon contact therewith. A portion of a liquid collection element may extend beyond a substrate arranged to support or engage the liquid collection element. In certain embodiments, a portion of one surface of a liquid collection element may be covered with a removable (e.g., hinged) cover arranged to provide a barrier to liquid contacting the second electrode from a face of the liquid collection element, but permitting lateral flow of saliva within the liquid collection element. Maintaining a portion of the liquid collection element isolated from surface contact with liquid reduces the possibility for liquid to reach a second (or subsequent) electrode or sensing element before the liquid collection element is saturated with saliva.

In certain embodiments, multiple portions of a liquid collection element may be exposed, with the exposed areas separated by one or more liquid impermeable barriers arranged to limit a tendency of an absorptive surface or portion of the liquid collection element from being blocked to further liquid flow (e.g., blocking by soft tissue below the tongue thereby sealing or restricting the liquid inlet within a subject's mouth). If provided, such a barrier is preferably raised relative to at least one surface of the liquid collection element. In one embodiment, a barrier comprises a cover defining multiple apertures.

In certain embodiments, a portion of a liquid collection element may be covered by a removable liquid-impermeable covering element, such as a removable adhesive tape or other covering element.

A liquid collection element may include one or more reduced dimension guide channel portions arranged between at least one first electrode or sensing element and the at least one second electrode or sensing element. The term "channel" in this context does not necessarily require an open space with the absence of material; instead, a reduced dimension guide channel portion may contain porous or fibrous material. Since it is advantageous to ensure that a liquid collection element is fully saturated with saliva before triggering a signal indicating such date, one or more reduced dimension guide channel portions may be used to reduce the possibility that a frontal edge of saliva advancing within a liquid collection element may reach a second electrode or sensing element before the liquid collection element is saturated.

In certain embodiments, a liquid collection element may include one or more tubes or channels that are devoid of porous or fibrous material. For example, a liquid collection element may include one or more microfluidic channels each having at least one dimension of less than about 500 microns. One or more flow regulating elements may be provided in a liquid collection element in order to reduce the possibility that a frontal edge of saliva advancing within a liquid collection element may reach a second electrode or sensing element before the liquid collection element is saturated.

In certain embodiments, a liquid collection element may be arranged within a sample collection portion of an apparatus for sensing state of euhydration or dehydration, with other components of the apparatus (e.g., timing element, processing element/comparator, and/or signaling element, among others) being arranged within a monitoring portion. In certain embodiments, a sampling portion may be operatively connected to a monitoring portion via an electrical communication cable and an electrical interface connector, or via wireless communication, thereby permitting the sampling portion to be inserted into the mouth of a user while a monitoring portion is spatially separated therefrom. In other embodiments, a sampling portion may be arranged for insertion into a monitoring portion (e.g., within a slot defined therein) to establish electrical and/or sensory communication between the sampling portion and a monitoring portion. By providing a sampling portion separate from the monitoring portion, the monitoring portion may be sequentially reused with numerous sampling portions of disposable character. A monitoring portion may be arranged to sense salivary secretion rate alone, or may be arranged to further sense concentration of at least one analyte in saliva such as with an optical reading element. A monitoring portion may include any suitable combination of various components such as (but not limited to) a battery, a timer, a processing and/or control element, a comparator, a memory, a display, one or more indicator lights, an audible output element, sensor traces or wires, an electrical interface plug, a sampling portion receiving cavity, an optical reading element, and a communication element arranged to communicate (whether in wired or wireless fashion) with one or more terminals or other remote communication devices.

In certain embodiments, an apparatus for sensing state of euhydration or dehydration is arranged to generate a user-perceptible output signal indicative of hydration status that is quantitative in character. A user perceptible output signal generated by such an apparatus may be visible, audible, and/or tactile in character. Examples of quantitative signals include salivary secretion rate (e.g., in $\mu$l/min or other suitable units, obtainable by dividing volumetric capacity of the liquid collection element over measured time to saturation), time to saturate the liquid collection element (e.g., in seconds), analyte concentration level (e.g., in $\mu$g/ml or other suitable units, obtainable via use of an optical reading element or by comparison of colored bands or colored position along an immunoassay test strip calibrated to one or more reference indicator values), and the like.

In certain embodiments, an apparatus for sensing state of euhydration or dehydration is arranged to generate a user-perceptible output signal indicative of hydration status that is qualitative in character. With respect to salivary secretion, one or more threshold values for salivary secretion rate or time to saturate a liquid collection element indicative of euhydration or dehydration may be stored in memory of the apparatus, and sensed values may be compared to the one or more threshold values to provide a simple qualitative assessment as to whether a user is in a state of euhydration or dehydration. A qualitative signal may be selected from two, three, four, or more possible results. For example, in certain embodiments, a qualitative signal may be limited to two possible results of euhydration or dehydration. In other embodiments, a qualitative signal may be selected from three possible results of euhydration, dehydration, and severe dehydration. In other embodiments, a qualitative signal may be selected from three possible results of euhydration, slight dehydration, moderate dehydration, and severe dehydration. With respect to concentration of one or more analytes in saliva, output of an optical reading element may be compared to one or more threshold signal level to provide a qualitative output. Alternatively, presence or absence of a colored signal within a window positioned at a specified distance from a conjugate pad of an immunoassay test strip (with a colored signal indicating high concentration of sensed salivary analyte) may provide a qualitative output (e.g., with presence of a colored signal indicating a dehydration state, and absence of a colored signal indicating a euhydration state). A processing element and/or comparator may be arranged to compare at least one time value against at least one predetermined threshold value, and/or to compare multiple time values against one another (or a value derived therefrom), and responsively trigger a signaling element to generate a user-perceptible qualitative signal indicative of state of euhydration, state of dehydration, or salivary secretion rate based at least in part on such comparison.

In certain embodiments, a hydration state sensing device may provide a quantitative output signal based on results of one salivary test method, and provide a qualitative output signal based on results of one salivary test method. For example, a device may provide a quantitative output signal indicative of salivary secretion rate, and provide a qualitative output signal indicative of analyte concentration (or vice-versa).

One or more user-perceptible output signals representing a quantitative and/or qualitative values may be generated by one or more signaling elements, such as (but not limited to) a LCD display, a LED array, an alphanumeric display, one or more lamps (e.g., LEDs), a sound generating device (e.g., a speaker), and/or a tactile signaling element such as a vibration generator. Multiple signaling elements may be provided. In certain embodiments, a sound generating device provides an output signal in the form of a synthesized voice.

In certain embodiments, a salivary stimulating agent is applied to a subject prior to or concurrent with placement of a liquid collection element (or portion thereof) in the subject's mouth, utilizing a device and method for sensing salivary secretion rate. In certain embodiments, a salivary stimulating agent may be coated on or otherwise administered to a user by a liquid collection element. A salivary stimulating agent may be arranged for gustatory and/or olfactory stimulation of saliva production. Examples of gustatory salivary stimulating agents include (but are not limited to) citric acid and sodium chloride. In one embodiment, a saliva stimulant coating may include citric acid (35-45%), sugarless sour candy (54%-64%) and sodium chloride (1%). Mechanical stimulation of saliva production (e.g., a mechanical salivary stimulating element) may also be used. In certain embodiments, a chewable article such as chewing gum is administered to a user prior to or concurrent with placement of a liquid collection element (or portion thereof) in a subject to mouth, in order to stimulate saliva production by chewing.

In certain embodiments, a salivary collection device comprising a chewable article is administered to a subject, to promote mechanical stimulation of saliva production (optionally in combination with one or more gustatory and/or olfactory salivary stimulating agents) and collection of saliva generated by the subject. Such a chewable article may comprise a salivary collection pad or other collection element. In certain embodiments, both a chewable article and a salivary collection pad are administered to the subject, whether in a simultaneous or sequential fashion, to stimulate saliva production and collection of the stimulated saliva. After stimulated saliva production and saliva collection is complete, a saliva collection element may be removed from the mouth of the subject, optionally subjected to one or more treatment steps (e.g., with buffer), and subjected to one or more analytical steps as described herein.

In certain embodiments, an apparatus for sensing state of euhydration, state of dehydration, or salivary secretion rate of a mammalian subject includes a substrate arranged to support or engage a liquid-permeable liquid collection element arranged to transport liquid by wicking, and having a predefined liquid holding capacity. The substrate has multiple electrical contact pairs including a first electrical contact pair and a (downstream) second electrical contact pair. The first electrical contact pair may be arranged to close a first electrical circuit upon exposure to saliva when the liquid collection element is placed in fluid communication with oral mucosa of the mammalian subject, and the second electrode pair is arranged to close a second electrical circuit upon exposure to saliva transported though at least a portion of the liquid collection element. A timing element may be arranged to receive a signal indicative of closure of the first electrical circuit, arranged to receive a signal indicative of closure of the second electrical circuit, and arranged to generate a first time value indicative of time elapsed between the closure of the second electrical circuit and the closure of the first electrical circuit. A signaling element may be arranged to generate an output signal indicative of state of euhydration, state of dehydration, or salivary secretion rate of the mammalian subject based at least in part on the first time value. In certain embodiments, one or more additional downstream electrical contact pairs may be provided, and migration of saliva to contact these downstream electrical contact pairs may be used to generate additional (e.g., second, third, fourth, etc.) time values, wherein the output signal may be based at least in part on the multiple time values, or on one or more signals derived from the multiple time values.

In certain embodiments, an apparatus for sensing a state of euhydration, state of dehydration, or salivary secretion rate of a mammalian subject includes a salivary stimulating agent, a liquid collection element, multiple electrodes or sensing elements, a timing element, and a signaling element. The liquid collection element is arranged for placement in fluid communication with oral mucosa of a user, may be liquid permeable, be arranged to transport liquid by wicking, and have a predefined liquid holding capacity. The salivary stimulating agent is arranged for placement into the mouth prior to or substantially concurrently with establishment of fluid communication between the liquid collection element and oral mucosa. At least one first electrode or sensing element is arranged to sense a condition indicative of exposure of a portion of the liquid collection element to oral mucosa, and at least one second electrode or sensing element arranged to sense a condition indicative of movement by saliva through at least a portion of the liquid collection element. The timing element may be initiated responsive to receipt of a signal from or detection of change of state of the (at least one) first electrode or sensing element, and generate a time value indicative of elapsed time since said initiation upon receipt of a signal from or detection of a change of state of the (at least one) second electrode or sensing element. The signaling element may generate an output signal indicative of state of euhydration, state of dehydration, or salivary secretion rate based at least in part on the time value. Such a device may be supplemented by at least one indicator or test region arranged to interact with one or more analytes in saliva of the user. An optical reading element may be arranged to generate an electrical signal correlative of concentration one or more analytes upon optical interaction with indicator or test region(s). A signal processing element may use at least one time value in combination with the electrical signal correlative of concentration one or more analytes to generate an output signal indicative of the hydration state or salivary secretion state.

In certain embodiments, a method for sensing hydration state or salivary secretion rate includes steps such as inserting a salivary stimulating agent into the mouth of the mammalian subject to stimulate saliva flow; placing at least a portion of a liquid collection element of predefined liquid holding volumetric capacity in contact with oral mucosa of the mammalian subject; detecting a condition indicative of presence of saliva on or adjacent to the liquid collection element upon exposure of the at least a portion of the liquid collection element to oral mucosa of the mammalian subject, and responsively starting a timer; detecting a condition indicative of movement of saliva through at least a portion of the liquid collection element while the at least a portion of the liquid collection element is exposed to oral mucosa of the mammalian subject, and responsively storing a time value indicative of elapsed time since the timer was started; and utilizing the time value to generate an output signal indicative of state of euhydration, state of dehydration, or salivary secretion rate of the mammalian subject. A condition indicative of movement of saliva through the liquid collection element may include detecting saturation of at least a portion or the entirety of the liquid collection element.

In certain embodiments, a first method for sensing a state of euhydration, state of dehydration, or salivary secretion rate is utilized, and based on the results of the first method, a second method sensing a state of euhydration or dehydration is applied may be utilized to validate the first method. For example, sensing of salivary secretion rate may be utilized first to provide results characterized by high sensitivity, but comparatively low specificity. Thereafter, sensing of concentration of at least one analyte in saliva may be utilized, to provide results of relatively high sensitivity, but comparatively higher specificity. Utilization of two distinct methods for sensing state of euhydration or dehydration provides a very high confidence level if results of the different methods are consistent.

In certain embodiments, at least one method for sensing a state of euhydration or dehydration as described herein is applied to a user according to a first testing step, one or more output values yielded from the first testing step is stored in a memory, then at least one method for sensing a state of euhydration or dehydration as described herein is applied to the same user according to a second testing step, and one or more output value yielded from the first testing step are compared to one or more stored values. Such steps may be periodically repeated as necessary to assess change in hydration state of the user.

In certain embodiments, a liquid collection element utilized for sensing salivary secretion rate may be provided in fluid communication with an immunochromatographic lateral flow test strip including at least one indicator or test region arranged to interact with at least one analyte in saliva obtained from the mammalian subject, so that a salivary analyte concentration in sensing method may be performed following the sensing of salivary secretion rate utilizing the same saliva sample. A conjugate pad (e.g., including monoclonal antibodies conjugated to gold nanoparticles) employed by an immunochromatographic assay for sensing salivary analyte concentration may be arranged between a liquid collection element and an immunochromatographic test strip.

In certain embodiments, a liquid collection element and an immunochromatographic test strip are arranged in or on a common substrate or housing. In other embodiments, a liquid collection element is associated with a first substrate or housing, and an immunochromatographic test strip is associated with a second substrate or housing. Following completion of a salivary secretion rate sensing method, a liquid collection pad may be treated with a buffer solution, and a buffered saliva composition may be supplied to an immunochromatographic test device. One potential benefit of such buffering is to mitigate variability in saliva samples (e.g., viscosity, tonicity, ionic strength, and/or pH) that may otherwise reduce reliability of an immunochromatographic assay.

In certain embodiments, an immunochromatographic lateral flow test strip includes a uniform layer of monoclonal antibodies adapted to bind a selected analyte in saliva. Examples of suitable analytes include (but are not limited to) IgA (e.g., secretory IgA, or SIgA), salivary albumin, secretory component, and salivary aldosterone, and while SIgA is mentioned hereafter, it is to be understood that any suitable analyte may be used. An immunochromatographic lateral flow test strip may be designed to bind a calibrated quantity of SIgA (e.g., using anti-SIgA) per millimeter of strip length. As saliva enters the strip, the SIgA is colorized by passing through a conjugate pad containing anti-SIgA conjugated to nano-gold particles which binds to the SIgA, imparting a color (e.g., pink) to the analyte. When all of the colored SIgA is bound to the strip, the remaining length of the strip remains white. Marks may be delineated by a cover optionally containing multiple holes that reveal the strip at various points along its length, with each pointing represents a total amount of SIgA per ml of saliva. Calibration marks may be arranged proximate to openings in the cover to permit quantitative assessment of analyte concentration based upon presence (or absence) of color in an adjacent window.

In certain embodiments, an immunochromatographic lateral flow test strip includes a series of antibody (e.g., anti-SIgA) bands arranged as stripes aligned perpendicular to a long dimension of the strip. Each stripe line has a specific (though not necessarily the same) analyte absorptive capacity. Thus, substantially the same method as articulated in the preceding paragraph can be accomplished using a series of striped bands rather than a uniform layer of antibodies for the selected analyte over the entire strip.

In certain embodiments, an immunochromatographic lateral flow test strip and cover are arranged to provide a positive control region (e.g., corresponding to a window defined in a cover over the strip) disposed downstream of a conjugate pad but upstream of one or more indicator windows providing quantitative or qualitative indication of hydration state. Colorization of such a positive control region (e.g., with pink color) will indicate that a liquid sample is present within the lateral flow test strip, that the conjugate pad is functional, and that the sample contains the analyte (or analytes) of interest. Presence of a colored signal in the positive control region increases confidence in quantitative or qualitative signals generated in downstream test windows.

In certain embodiments, one or more immunochromatographic lateral flow test strips or portions thereof within the same apparatus may include different monoclonal antibodies arranged to bind different analytes. In certain embodiments, an immunochromatographic lateral flow test strip includes a first group of monoclonal antibodies arranged to interact with a first analyte selected from IgA, albumin, secretory component, and aldosterone, and a second group of different monoclonal antibodies arranged to interact with a second analyte selected from IgA, albumin, secretory component, and aldosterone, wherein the second analyte differs from the first analyte. Different antibodies arranged to interact with different analytes may be provided in one or more of same test or indicator regions located along a single immunochromatographic lateral flow test strip, may be provided in different test or indicator regions located along parallel flow paths in a single immunochromatographic lateral flow test strip, or may be provided in different test or indicator regions located in multiple immunochromatographic lateral flow test strips arranged in parallel within a single device or system. Different analytes may be colored differently (e.g., blue and yellow) via one or more conjugate pads. Signals based upon a combination of different analytes bound in the same region may be combined (e.g., blue and yellow combined to make a green color). Immunochromatographic lateral flow test strips arranged to interact with multiple analytes may be arranged to perform different assay formats, such as a competitive binding assay format or a sandwich assay format.

In certain embodiments, at least one of oral fluids, intravenous fluids, electrolytes, medication, and medical treatment is administered to a user based on one or more output signals generated by hydration state sensing devices and methods as described herein. In certain embodiments, an output signal from an apparatus as described herein may be communicated (e.g., via wired or wireless communication) to an administering element to facilitate automated administration of at least one of oral fluids, intravenous fluids, electrolytes, medication, and medical treatment of fluids without human intervention.

In certain embodiments, operation of one or more sensing methods or processing of results thereof may be affected by one or more signals received from a user input element. In various embodiments, a user input element may be used to store one or more sensed values, to compare one or more currently sensed values to one or more stored values corresponding to previously sensed values, and/or to select a user population of which the user is a member. To the extent that user population status (e.g., age, sex, disease state, medication usage, activity level, or the like) may affect comparison values used to provide qualitative assessments, user input information may be used to adjust or select appropriate comparison values to as a basis for providing a qualitative output signal.

Referring to the figures, is a schematic diagram showing interconnection of various components of a system 100 for sensing a state of euhydration or dehydration of a subject via saliva of the subject is illustrated in FIG. 1. A liquid collection element and/or interface 101 includes multiple electrodes or sensors 121, 122 that may be arranged to sense a condition indicative of exposure of the liquid collection element to oral mucosa, and to sense a condition indicative of saturation of the predefined liquid holding capacity of the liquid collection element. Such electrodes or sensors 121, 122 may therefore be used to automatically start and stop a timing element (e.g., a timer) to generate a time value correlative of salivary secretion rate. The electrodes or sensors 121, 122 are arranged in electrical communication with a processing/control element 170 having an associated battery 171 and a memory 172. In certain embodiments, the processing/control element 170 comprises a microprocessor arranged to execute a predefined machine-readable instruction set. The processing/control element 170 may provide timing functionality, or a separate timer (not shown) may be used. A signaling or output element 150, which may be embodied in a display, is arranged in electrical communication with the processing/control element 170. A reading element 173 such as an optical reader may be arranged in communication with the processing/control element 170. The processing/control element 170 may receive user input signals from a user input element 175. A communication element 195, such as may be embodied in a wired interface (e.g., a plug or socket) and/or wireless interface (e.g., a transmitter or transceiver), may be arranged to permit communication and signals between the processing/control element 170 and at least one terminal or remote communication device 196. In this manner, signals indicative of state of euhydration or dehydration of a user may be monitored and logged remotely (e.g., at a nurse's station or a sport manager's communication device), and actions may be taken responsive to such signals. In certain embodiments, a terminal or remote communication device 196 arranged to receive signals indicative of state of euhydration or dehydration may be worn by a user while participating in an athletic event.

FIG. 2 is a side cross-sectional schematic view of a portion of a saliva collection element 210 arranged in contact with an interface portion 201 of a hydration state sensing device according to certain embodiments of the present invention. A body structure 231 includes a substrate 230 arranged to support the saliva collection element 210, and includes a cover portion 232 is pivotally mounted to the body structure 231 with a hinge 232A. A first pair of electrodes 221A, 221B with a gap 223 therebetween is arranged proximate to a first end 211 of the saliva collection element 210, and a second electrode or electrode pair 222A is arranged proximate to a second end 212 of the saliva collection element 210. A first portion 213 of the saliva collection element 210 proximate to the first end 211 is exposed to receive and absorb saliva when the first end 211 is placed into the mouth of a user to contact oral mucosa. A second portion 214 of the saliva collection element 210 proximate to the second end 212 is covered with the cover element 232. This covering arrangement ensures that liquid can only reach the second electrode or electrode pair 222A by lateral flow through the saliva collection element 210. The electrodes 221A, 221B, 222A may be formed in or on the substrate 230 with suitable electrical traces (not shown) providing electrical communication with a processing or control element. The first set of electrodes 221A, 221B may be defined through one or both surfaces of the substrate 230, whereas the second electrode or electrode pair 222A is preferably only accessible to liquid by lateral flow through the saliva collection element 210. The saliva collection element 210 may be adhered or otherwise affixed to the substrate 230. One or more portions of the substrate 230 proximate to the first portion 213 may define openings (not shown) or be liquid permeable to permit saliva to contact the saliva collection element 210.

FIG. 3 is a side cross-sectional schematic view of a saliva collection element 310 having integral electrodes 321A, 321B, 322A, and a backing element 318 and a covering element 319, with a sandwiched layer portion 314 arranged between the backing element 318 and the covering element 319, and with an exposed layer portion 313 supported above the backing element 318. A first pair of electrodes 321A, 321B separated by a gap 323 is arranged proximate to a first end 313 of the saliva collection element 310, and a second electrode or electrode pair 322A is arranged proximate to a second end 312 of the saliva collection element 310. The saliva collection element 210 may be mechanically supported by a supporting substrate (not shown), or may be retained within a body structure (not shown) proximate to the second end 312.

FIG. 4 is a top plan schematic view of a saliva collection element 410 having integral electrodes with a guide channel portion 426 arranged between two electrode pairs 421A-421B, 422A-422B. The first electrode pair 421A-421B is separated by a first gap 423, and the second electrode pair 422A-422B is separated by a second gap 424. The guide channel portion 426 includes a channel of reducing width (e.g., roughly triangular in shape) defined by boundary regions 427 treated with hydrophobic or water-impermeable material such as adhesive, wax, or the like. The function of the guide channel portion 426 is to prevent premature triggering of an output signal by the second electrode pair 422A-422B. That is, such guide channel portion 426 serves to guide a frontal edge of saliva advancing within the saliva collection element 410 in order to promote saturation of the saliva collection element 410 with saliva before the second electrode pair 422A-422B generates a signal indicating such saturated condition has been attained.

Although various electrode configurations have been shown, it is to be appreciated that any suitable positioning of electrodes relative to a saliva (or liquid) collection element may be employed. Moreover, any of various suitable types of sensors may be utilized instead of or in addition to such electrodes.

FIG. 5 is a top cross-sectional schematic view of a device 500 for sensing a state of euhydration or dehydration of a subject utilizing saliva according to certain embodiments of the present invention, with the device 500 arranged to sense both salivary secretion rate and concentration of at least one analyte in saliva. The device 500 includes a liquid collection element 510 with a first pair of electrodes 521A-521B arranged to detect insertion of a first end 511 of the liquid collection element 510 into a user's mouth (with insertion of the device 500 into a user's mouth being limited by a mouth insertion shield 533), and a second pair of electrodes 522A-522B arranged to detect migration (e.g., wicking) of saliva to a second end 512 of the liquid collection element 510 as indicative of a condition of saturation thereof. The second end 512 of the liquid collection element 510 is preferably arranged within a body structure 531 to ensure that saliva reaches the second end 512 only by lateral migration through the liquid collection element 510. First and second electrical traces 581, 582 provide electrical communication between a processing or control element (not shown) associated with the device 500 and the electrode pairs 521A-521B, 522A-522B. A signaling element 550 in the form of a display is arranged to receive time value signals from a timer (not shown) operatively connected to the first and second electrode pairs 521A-521B, 522A-522B and to provide a user-perceptible signal quantifying salivary secretion rate (e.g., as an alphanumeric value).

When the salivary secretion rate sensing is complete, the device 500 preferably generates a user-perceptible signal (e.g., audible and/or visible) prompting the user to place the liquid collection device 510 (still attached to the device 500) into a tube or other container of buffer solution (not shown). The liquid collection element 510 is in fluid communication with a downstream immunochromatographic lateral flow strip 540. Buffered saliva flows by wicking through a transition zone 534 past the second electrode pair 522A-522B to contact a conjugate pad 535 including monoclonal antibodies conjugated to gold nanoparticles, thereby imparting pink color to the analyte. As saliva continues to flow through the lateral flow strip 540 in a direction toward a distal end 599 of the device 500, the colored analyte is absorbed by the strip 540 to impart color to the strip 540. When all of the colored analyte is bound to the strip 540, any remaining length of the strip 540 remains white in color. As saliva progresses through the strip 540 toward the distal end 599 and analyte in the saliva is bound to the strip 540, colorization of the strip may be progressively lighter in color in a direction toward the distal end 599. The higher the concentration of target analyte present in the saliva, the greater extent of the strip 540 will be colorized. Test or indicator regions 541-545 having a progressive gradation in color from pink to white following completion of the immunoassay are arranged along the length of the strip 540. Such test or indicator regions 541-545 may constitute discrete regions (e.g., stripes arranged perpendicular to the length of the strip 540) of monoclonal antibodies, or may constitute portions of a strip 540 uniformly coated with monoclonal antibodies that are exposed via windows (not shown) defined in a cover portion of the body 531. Calibration marks are provided adjacent to (i.e., to the right of) the test or indicator regions 541-545, to enable concentration of analyte in the saliva to be quantified. A third pair of electrodes 548A-548B with associated electrical traces 588 are arranged at the end of the lateral flow strip 540 to detect presence of saliva as indicative of the end of the immunoassay. The device 500 therefore enables quantification of both salivary flow rate and salivary analyte concentration, with each being correlative of state of euhydration or dehydration of the user.

FIG. 6 is a top plan schematic view of a second device 600 (similar to the apparatus of FIG. 5) for sensing a state of euhydration or dehydration of a subject utilizing saliva. The device 600 operates in a manner substantially the same as the device 500, but includes additional signaling elements 651-653 arranged along one end 699 proximate to the display 650 to aid in operation of the device 600. The device 600 includes a liquid collection element 610 extending into a body structure 631 and having an end 611 adapted for insertion in the mouth of a user, with insertion of the device 600 into a user's mouth being limited by a mouth insertion shield 633. The body or housing 631, which is preferably opaque in character, includes a series of window 661-665 permitting viewing of the test or indicator regions 641-645. In operation of the device 600, the liquid collection element 610 is placed into the mouth of a user to initiate collection of saliva for sensing of salivary secretion rate. A first signaling element 651 (e.g., green LED) is activated to signal contact of the liquid collection element 610 with the oral mucosa under the user's tongue. When the liquid collection element 610 is saturated (filled) with saliva, a second signaling element 652 (e.g., yellow LED) is activated to signify that saliva collection is complete, and that the liquid collection element 610 should be removed from the user's mouth and placed into a buffer solution (not shown). A lateral flow strip internal to the body or housing 631 is used to perform an immunochromatographic assay to sense concentration of at least one analyte in the (buffered) saliva, including flow of the buffered saliva past the test or indicator regions 641-645 as visible through the windows 661-665. When the immunochromatographic lateral flow assay is complete, a third signaling element 653 (e.g., red LED) is activated to signify completion of same. Such signaling elements 651-653 provide user feedback as to operational state and prompt the user when one action is completed (and another action should be initiated). It is to be appreciated that non-visual signaling elements such as audible or tactile signaling elements may additionally or alternatively be used.

In certain embodiments, a device for sensing a state of euhydration or dehydration of a subject utilizing saliva may provide one or more qualitative assessments of hydration status. For example, referring to FIG. 7, a device 700 arranged to sense both salivary secretion rate and concentration of at least one analyte in saliva, to provide a qualitative output signal based on salivary secretion rate (e.g., in comparison to one or more stored or predefined values indicative of salivary secretion rate), and to provide a qualitative signal based on analyte concentration (e.g., in comparison to one or more stored or predefined values indicative of analyte concentration). The device 700 includes a liquid collection element 710 with a first pair of electrodes 721A-721B arranged to detect insertion of a first end 711 of the liquid collection element 710 into a user's mouth (with insertion of the device 700 into a user's mouth being limited by a mouth insertion shield 733), and a second pair of electrodes 722A-722B arranged to detect migration (e.g., wicking) of saliva to a second end 712 of the liquid collection element 710 as indicative of a condition of saturation thereof. The second end 712 of the liquid collection element 710 is preferably arranged within a body structure 731 to ensure that saliva reaches the second end 712 only by lateral migration through the liquid collection element 710. First and second electrical traces 781, 782 provide electrical communication between a processing or control element (not shown) associated with the device 700 and the electrode pairs 721A-721B, 722A-722B. A signaling element 750 in the form of a display is arranged to receive time value signals from a timer (not shown) operatively connected to the first and second electrode pairs 721A-721B, 722A-722B and to provide a user-perceptible qualitative signal (e.g., audible and/or visible signal) indicating whether salivary secretion rate is consistent with a specific hydration state, such as euhydration or dehydration. In certain embodiments, a visible signal is provided by a display element (e.g., display 750) arranged to display a "+" symbol if the user's salivary flow rate is consistent with a state of dehydration, and a "−" symbol if the user's salivary flow rate is consistent with a state of euhydration.

When the salivary secretion rate sensing is complete, the device 700 preferably generates a user-perceptible signal (e.g., audible and/or visible) prompting the user to place the liquid collection device 710 (still attached to the device 700) into a tube or other container of buffer solution (not shown). The liquid collection element 710 is in fluid communication with a downstream immunochromatographic lateral flow strip 740 arranged within a body structure 731 of the device 700. Buffered saliva flows by wicking through a transition zone 734 past the second electrode pair 722A-722B to contact a conjugate pad 735 including monoclonal antibodies conjugated to gold nanoparticles, thereby imparting pink color to the analyte. As saliva continues to flow through the lateral flow strip 740 in a direction toward a distal end 799 of the device 700, the colored analyte is absorbed by the strip 740 to impart color to the strip 740. A positive control region 741 (e.g., corresponding to a window defined in a cover portion of the body structure 731) including monoclonal antibodies arranged to bind the colored analyte is arranged downstream of the conjugate pad 735. Colorization of the positive control region 741 (e.g., with pink color) will indicate that a liquid sample is present within the lateral flow test strip, that the conjugate pad is functional, and that the sample contains the analyte (or analytes) of interest. Downstream of the positive control region 741 is a test region 742 arranged to bind colored analyte in the buffered saliva, if such analyte is present at the position of the test region 742. That is, between the control region 741 and the test region 742 are additional monoclonal antibodies arranged to bind the colored analyte, and depending on the initial concentration of the analyte in the saliva, there may or may not be sufficient analyte remaining in the sample to colorize the test region 742. Presence of a color (e.g., pink) in the test region 742 indicates that a relatively high concentration of analyte was originally present in the saliva sample collected by the liquid collection element 710, whereas lack of non-white color in the test region 742 indicates that a relative low concentration of analyte was originally presented in the saliva sample. The test region 742 therefore provides a qualitative signal correlative of state of euhydration or dehydration. Various parameters such as spacing between the control region 741 and the test region 742; amount of monoclonal antibody present at the control region, at the test region 742, and between the control region 741 and the test region 742; concentration or amount of coloring agent in the conjugate pad 735; and so on may be adjusted to provide an appropriate signal discrimination level at the control region 742. Each of the positive control region 741 and the test region 742 may have an associated window (not shown) defined in the body structure 731 to reveal the regions 741, 742 for visual inspection thereof without revealing a portion of the test strip 740 disposed therebetween. A third pair of electrodes 748A-748B with associated electrical traces 788 are arranged at the end of the lateral flow strip 740 to detect presence of saliva as indicative of the end of the immunoassay. The device 700 therefore provides qualitative signals for each of salivary flow rate and salivary analyte concentration, with each being correlative of state of euhydration or dehydration of the user. It is to be appreciated that the device 700 may be modified to provide quantitative signals for salivary secretion rate, and/or subjected to further analysis (e.g., using an optical reader arranged to interact with the test region 742 (or the test region 742 in combination with the control region 741) to provide quantitative signals for analyte concentration.

FIG. 8 is a top plan schematic view of another device 800 (similar to the apparatus of FIG. 7) for providing qualitative signals indicative of a state of euhydration or dehydration of a subject utilizing saliva, by sensing salivary secretion rate and concentration of at least one analyte in saliva. The device 800 operates in a manner substantially the same as the previously-described device 700, but includes additional signaling elements 851-853 arranged along a distal end 899 proximate to the display 850 to aid in operation of the device 800. The device 800 includes a liquid collection element 810 extending into a body structure 831 and having an end 811 adapted for insertion in the mouth of a user, with insertion of the device 800 into a user's mouth being limited by a mouth insertion shield 833. The body or housing 831, which is preferably opaque in character, includes a first window 861 arranged to permit viewing of an immunochromatographic positive control region 841, and includes a second window 862 arranged to permit viewing of an immunochromatographic test or indicator region 862. In operation of the device 800, the liquid collection element 810 is placed into the mouth of a user to initiate collection of saliva for sensing of salivary secretion rate. A first signaling element 851 (e.g., green LED) is activated to signal contact of the liquid collection element 810 with the oral mucosa under the user's tongue. When the liquid collection element 810 is saturated (filled) with saliva, a second signaling element 852 (e.g., yellow LED) is activated to signify that saliva collection is complete, and that the liquid collection element 810 should be removed from the user's mouth and placed into a buffer solution (not shown). An lateral flow strip internal to the body or housing 831 is used to perform an immunochromatographic assay to sense concentration of at least one analyte in the (buffered) saliva, including flow of the saliva past the control region 841 (visible through a first window 861 defined in the body or housing 831) and past the test or indicator region 842 (visible through a second window 862 defined in the body or housing 831). Presence of a non-white colored (e.g., pink) signal in the test or indicator region 842 indicates high concentration of analyte (e.g., IgA, albumin, secretory component, or aldosterone) in the saliva, indicating that the user is in a dehydrated state. When the immunochromatographic lateral flow assay is complete, a third signaling element 853 (e.g., red LED) is activated to signify completion of same. Another signaling element 854 may be provided for auditory signaling corresponding to any of the foregoing conditions, and/or to provide visible signaling of further information such as device state, battery status, etc. Such signaling elements 851-854 provide user feedback as to operational state and prompt the user when one action is completed (and another action should be initiated).

In certain embodiments, a device for sensing a state of euhydration or dehydration of a subject utilizing saliva may include a sampling portion that is removably insertable into a monitoring portion for use in collecting and analyzing saliva.

FIGS. 9A-9B illustrate a sampling portion 900A and a monitoring portion 900B of an apparatus 900 for sensing a state of euhydration or dehydration utilizing saliva of a user. FIG. 9A illustrates the sampling portion 900A arranged proximate to a tube 908 containing buffer solution 909. The sampling portion 900A includes a liquid collection element 910 arranged along a proximal end 911, and a body or housing 934 arranged to retain an opposite end of the liquid collection element 910. The sampling portion 900A further includes a mouth insertion shield 933 arranged to limit insertion of the sampling portion 900A into a user's mouth, and an immunochromatographic lateral flow strip 940 arranged downstream of the liquid collection element 910. The sampling portion 900A is designed as a single (disposable) use element, with a distal end 949 and lateral flow strip 940 of the sampling portion 900A being arranged for insertion through an opening 967 (at a first end 998 of the monitoring portion 900B) into a slot or recess 968 defined in a monitoring portion 900B, as shown in FIG. 9B.

The monitoring portion 900B is designed to be sequentially reused with different disposable sampling portions 900A. The monitoring portion 900B includes a signaling element 950 in the form of a display arranged to receive time value signals from a timer (not shown), and additional signaling elements 951-954, such as may comprise LEDs and/or audible output elements. Electrodes and/or sensors (not shown) arranged in, on, or adjacent to the sampling portion are in electrical communication with a processing/control element (not shown) of the monitoring portion 900B to sense (a) a condition indicative of insertion of the liquid collection element 910 into the mouth of a user in contact with oral mucosa, (b) a condition indicative of saturation of the liquid collection element 910, and (c) a condition indicative of saliva reaching a distal end of the lateral flow strip 940 (at or near the distal end 949 of the sampling portion 900). The monitoring portion 900B further includes elements 961, 962 which may comprise windows or optical reading elements arranged for interaction with the immunochromatographic lateral flow strip 940. A first element 961 may be arranged proximate to a positive control region of the strip 940, and a second element 962 may be arranged proximate to a test or indication region of the strip 940.

In operation, the distal end 949 and lateral flow strip 940 of the sampling portion are inserted through an opening 967 at a first end 998 of the monitoring portion 900B into a recess or slot 968 defined therein, to facilitate electrical and/or sensory communication between the sampling portion 900A and the monitoring portion 900B. With the sampling portion 900A and the monitoring portion 900B so coupled, the liquid collection element 910 along a first end 911 of the sampling portion 900A is inserted into the mouth of a user to contact oral mucosa (e.g., under the user's tongue). One or more first electrodes and/or sensors associated with the liquid collection element 910 sense initiation of absorption of saliva by the liquid collection element 910 and one or more second electrodes and/or sensors (e.g., arranged within a body or housing 934 of the sampling portion 900A) sense a condition indicating that the liquid collection element 910 is saturated (e.g., filled to predefined volumetric capacity) with saliva. A first signaling element 951 may signal initiation of absorption of saliva by the liquid collection element 910, and a second signaling element 912 may signal saturation of the liquid collection element 910. A time value corresponding to the duration required to saturate the liquid collection element 910 may be used to determine salivary secretion rate, and a corresponding quantitative value or qualitative determination may be output by the display 950. After the salivary secretion rate sensing is complete, the user may be prompted (e.g., by the second signaling element 952 and/or an auditory tone) to place the liquid collection element 910 along the first end 911 into a buffer solution for treatment of saliva within liquid collection element 910. In certain embodiments, the sampling portion 900B may be retained within the monitoring portion 900B during the buffer treatment step; alternatively, the sampling portion 900A may be removed from the monitoring portion 900B during such buffer treatment (such as depicted in FIG. 9A) and then reinserted into the monitoring portion 900B for interpreting or reading results of an immunochromatographic assay performed with the lateral flow strip 940 to determine concentration of at least one analyte in saliva collected from the user. In certain embodiments, the monitoring portion 900B includes elements 961, 962 in the form of windows arranged to permit viewing of a positive control region and a test or indication region, respectively, of the lateral flow strip 940. In other embodiments, one or both elements 961, 962 of the monitoring portion 900B embodying at least one optical readers to assess presence of color at selected portions (e.g., a positive control region and a test or indication region) of the lateral flow strip 940. If at least one element 961, 962 comprises an optical reader, then output of such a reader may be displayed (e.g., in quantitative or qualitative fashion) using the display element 950. Results of the salivary secretion rate sensing and the salivary analyte concentration sensing may be stored and/or compared to one another, and results of such comparison may be displayed to the user using the display element 950. The device 900 resulting from the combination of the sampling portion 900A and the monitoring potion 900B therefore enables consideration of both salivary secretion rate sensing and salivary analyte concentration sensing to determine state of euhydration or dehydration of a user.

In certain embodiments, separate sampling and monitoring portions of a hydration state sensing apparatus may be connected via an electrical cable during a salivary secretion rate sensing step, and the sampling portion may be inserted into the monitoring portion for reading results of a subsequent immunochromatographic assay step for determining concentration of at least one analyte in the saliva. Referring to FIG. 10, a hydration state sensing apparatus 1000 includes a sampling portion 1000A and a monitoring portion 1000B connected via an electrical communication cable 1058 having associated interface plugs or connectors 1057, 1059. The sampling portion 1000A is intended for disposable one-time use, whereas the monitoring portion 1000B is intended to be re-used with different sampling portions 1000A. A processing/control element, battery, and timing element (not shown) associated with the monitoring portion 1000B may be provided in electrical communication with electrodes and/or sensors (not shown) of the sampling portion 1000A via the electrical interface cable 1058. The sampling portion 1000A includes a liquid collection element 1010 arranged along a proximal end 1011, and a body or housing 1034 arranged to retain an opposite end of the liquid collection element 1010. The sampling portion 1000A further includes a mouth insertion shield 1033 and an immunochromatographic lateral flow strip 1040 arranged downstream of the liquid collection element 1010. In one embodiment, the mouth insertion shield is movable, since the appropriate length of insertion of a portion of a sampling portion may depend on oral cavity size of the user. An interface plug or connector 1057 is arranged proximate to a distal end 1049 of the sampling portion 1000A. The monitoring portion includes first end 1098 and a second end 1099. The monitoring portion 1000B includes a signaling element 1050 which may comprise a display, and additional signaling elements 1051-1054 which may comprises visual or auditory signaling elements. The monitoring portion 1000B includes an opening 1067 arranged at a first end 1098 and arranged to receive the distal end 1049 of the sampling portion 1000A for insertion into a slot or recess 1068 defined in the monitoring portion 1000B. In certain embodiments, the monitoring portion 1000B includes elements 1061, 1062 in the form of windows arranged to permit viewing of a positive control region and a test or indication region, respectively, of the lateral flow strip 1040. In other embodiments, one or both elements 1061, 1062 of the monitoring portion 1000B embodying at least one optical readers to assess presence of color at selected portions (e.g., a positive control region and a test or indication region) of the lateral flow strip 1040.

In operation, the sampling portion 1000A and the monitoring portion 1000B are initially coupled via the electrical communication cable 1058 and associated plugs or connectors 1058-1059. The liquid collection element 1010 along a first end 1011 of the sampling portion 1000A is inserted into the mouth of a user to contact oral mucosa (e.g., under the user's tongue). One or more first electrodes and/or sensors associated with the liquid collection element 1010 sense initiation of absorption of saliva by the liquid collection element 1010 and one or more second electrodes and/or sensors (e.g., arranged within a body or housing 1034 of the sampling portion 1000A) sense a condition indicating that the liquid collection element 1010 is saturated (e.g., filled to predefined volumetric capacity) with saliva. A first signaling element 1051 may signal initiation of absorption of saliva by the liquid collection element 1010, and a second signaling element 1012 may signal saturation of the liquid collection element 1010. A time value corresponding to the duration required to saturate the liquid collection element 1010 may be used to determine salivary secretion rate, and a corresponding quantitative value or qualitative determination may be output by the display 1050. After the salivary secretion rate sensing is complete, the user may be prompted (e.g., by the second signaling element 1052 and/or an auditory tone) to place the liquid collection element 1010 along the first end 1011 into a buffer solution (not shown) for treatment of saliva within liquid collection element 1010. Thereafter, the sampling portion 1000A may be disconnected from the cable 1058 by removal of the plug or connector 1057, and the distal end 1049 of the sampling portion may be inserted via the opening 1067 into the slot or recess 1068 of the monitoring portion 1000B for interpretation or reading of the results of the immunochromatographic assay performed in the lateral flow strip 1040 as aided by the elements 1061, 1062 (e.g., in the form of windows or optical reading elements). The apparatus 1000 therefore provides both salivary secretion rate sensing and salivary analyte concentration sensing utility, to permit assessment of state of euhydration or dehydration of a user.

In certain embodiments, a system for sensing salivary secretion rate and salivary analyte concentration may utilize a first apparatus for salivary secretion rate sensing and a second apparatus for salivary analyte concentration sensing. FIG. 11A illustrates a salivary secretion rate sensing apparatus 1000 of a system for sensing a state of euhydration or dehydration of user, and FIG. 11B illustrates a salivary analyte concentration sensing apparatus 1195 of such system. The salivary secretion rate sensing apparatus 1100 includes a sampling portion 1100A and a monitoring portion 1100B connected via an electrical communication cable 1158 and associated plugs or connectors 1157, 1159. The sampling portion 1100 includes a liquid collection element 1110 arranged along a proximal end 1111, and a body or housing 1034 arranged to retain an opposite end of the liquid collection element 1010, with an tubular extension 1132 extending from the body or housing 1034 to contact one plug or connector 1157. A processing/control element, battery, and timing element (not shown) associated with the monitoring portion 1100B may be provided in electrical communication with electrodes and/or sensors (not shown) of the sampling portion 1100A via the electrical interface cable 1158. The monitoring portion 1100B further includes a display 1150 and first and second signaling elements 1151, 1152.

The salivary analyte concentration sensing apparatus 1195 includes a body or housing 1196 with a liquid collection element 1192 arranged at one end 1191, a conjugate pad 1135 downstream of the liquid collection element 1192, and an immunochromatographic lateral flow strip 1140 downstream of the conjugate pad 1135. A positive control region 1141 having an associated first window 1140 is provided downstream of the conjugate pad 1135, and a test or indication region 1142 having an associated second window 1162 downstream of the positive control region 1141 as liquid flows within the strip 1140 toward a distal end 1199 of the apparatus 1195.

In operation, the liquid collection element 1110 of the sampling portion 1100A of the salivary secretion rate apparatus 1000 is inserted into the mouth of a user, and a timer (e.g., contained within the monitoring portion 11008) is automatically started upon detection by at least one first sensor or electrode associated with the liquid collection element 1110. When the liquid collection element 1110 is saturated with saliva, at least one first sensor or electrode associated with the liquid collection element 1110 senses such condition and causes the timer to stop. Salivary secretion rate may be determined by dividing the resulting time value from the predefined volumetric capacity of the liquid collection element 1110. Signaling elements 1151, 1152 may signal starting and stopping of liquid collection, and either quantitative or qualitative output signals based on salivary secretion rate may be output via the display 1150. Thereafter, concentration of at least one analyte in the user's saliva may be sensed via the salivary analyte concentration sensing apparatus 1195.

In certain embodiments, the liquid collection element 1110 of the sampling portion is placed into, or otherwise washed or exuded (e.g., by squeezing or wringing) into a buffer, such as buffer 1109 in tube 1108. In other embodiments, the liquid collection element 1110 of the sampling portion 1100A is removed and placed into the housing 1196 of the salivary analyte concentration sensing apparatus 1195 to serve as the liquid collection element 1191 thereof, and then treated with buffer solution 1109. In other embodiments, the liquid collection element 1110 of the sampling portion 1110 is placed into contact with the liquid collection element 1192 of the of the salivary analyte concentration sensing apparatus 1195 (e.g., and optionally pressed) to transfer saliva into to the liquid collection element 1192, followed by treatment with buffer solution 1109. In other embodiments, a dedicated liquid collection element 1192 associated with the salivary analyte concentration sensing apparatus 1195 is placed into the user's mouth to gather a saliva sample, and the saliva-containing liquid collection element 1192 may be treated with buffer solution 1109, After saliva is present in the liquid collection element 1191 and buffered, the buffered saliva travels by wicking through a conjugate pad 1135 and into the immunochromatographic lateral flow strip, past the positive control region 1141 and the test or indication region 1142. As indicated previously, presence of color in the test or indication region 1142 indicates high salivary analyte concentration, which may indicate a state of dehydration of the user.

In certain embodiments, saliva production of a mammalian subject is stimulated, collected, and analyzed, such as to determine presence and/or concentration of at least one analyte in the collected saliva, as may be used to sense a state of euhydration or dehydration of the subject. In certain embodiments, presence and/or concentration of multiple analytes may be sensed, and signals correlative of presence and/or concentration of different analytes may be compared to provide an indication of state of euhydration or dehydration. Any one or more analytes in saliva may be used. In certain embodiments, at least one analyte subject to detection may include any of IgA, albumin, secretory component, and aldosterone.

Stimulation of production of saliva may include administering a gustatory salivary stimulating agent to the subject, administering an olfactory salivary stimulating agent to the subject, and/or use of a mechanical salivary stimulating agent (e.g. a chewable article) by the subject. In certain embodiments, multiple salivary stimulating means may be utilized in simultaneous or sequential fashion. Stimulated saliva may be collected by any suitable saliva collection element. In certain embodiments, a saliva collection element is inserted into the mouth of the subject to contact oral mucosa. Collected saliva may be treated prior to the performance of one or more analytical steps utilizing at least a portion of the saliva. Such treatment may include treatment with at least one buffer (e.g., buffer solution, such as may mitigate variability in characteristics such as viscosity, tonicity, ionic strength, and/or pH of raw saliva).

Sensing presence and/or concentration of at least one analyte in the collected saliva may be performed with any suitable analytical device. In certain embodiments, such analysis is performed with an immunochromatographic lateral flow test strip. In certain embodiments, an optical property of at least one indicator or test region of an analytical device containing at least a portion of the collected saliva may be analyzed, such as with an optical reader. In various embodiments, an analyte detection signal comprise a user-perceptible qualitative and/or quantitative signal. In certain embodiments, an analyte detection signal may be compared to at least one predetermined reference value and/or threshold value (with such values optionally being correlated to, or corrected for, one or more attributes of the user, such as age, health condition, drug intake, fluid intake, and so on), with such comparison being used to assess state of euhydration or dehydration of the mammalian subject. At least one of oral fluids, intravenous fluids, electrolytes, medication, and medical treatment may be administered to a mammalian subject based on an analyte detection signal.

In certain embodiments, analysis of presence and/or concentration of at least one analyte in collected saliva produced with the aid of saliva production stimulation means is validated with sensing of saliva production rate as disclosed previously herein. For example, an analyte presence and/or concentration analysis may be preceded or followed by steps including placing at least a portion of a liquid collection element of predefined liquid holding volumetric capacity in the mouth of the mammalian subject and starting a timer substantially simultaneously with exposure of the at least a portion of the liquid collection element to oral mucosa of the mammalian subject, and sensing a condition indicative of saturation of the predefined liquid holding capacity of the liquid collection element while the at least a portion of the liquid collection element is exposed to oral mucosa of the mammalian subject, and storing a time value indicative of elapsed time since the timer was started. An analyte detection value may be used in combination with a time value obtained from the foregoing process to assess state of euhydration or dehydration of a mammalian subject.

FIG. 15 provides a flowchart of various steps that may be employed in analyzing presence and/or concentration of at least one analyte in collected saliva produced with the aid of saliva production stimulation means. Block 1502 involves the step of stimulating production of saliva. As indicated previously, such stimulation may include administering a gustatory salivary stimulating agent to the subject, administering an olfactory salivary stimulating agent to the subject, and/or use of a mechanical salivary stimulating agent (e.g. a chewable article) by the subject. Block 1504 involves collection of stimulated saliva. Any suitable saliva collection element may be used, including but not limited to a saliva collection element arranged for placement in contact with oral mucosa of a mammalian subject. Such saliva collection for purposes of analyte detection may simultaneously be used for sensing of saliva production rate. Block 1506 involves analysis of presence and/or concentration of one or more analytes in the collected saliva. Any suitable analytical means as disclosed herein or otherwise known in the art may be used. Block 1508 involves comparison of sensed analyte concentration(s) or analyte presence to one or more previously sensed values or signals. Steps recited in (optional) block 1510 may be performed responsive to steps performed in block 1506 and/or block 1508, and involve storage of data generated by the sensing and/or comparison steps, or processed data derived therefrom. Stored values may be used to detect trends, and also used to generate alarms and/or reports. Steps recited in (optional) block 1512 may be performed responsive to steps performed in blocks 1508 or 1510, and involve performance of validation and/or follow-up tests. A validation test may involve use of a different analyte, different analytical technique, and/or different test methodology in comparison to an initial test. For example, an initial test involving steps recited in blocks 1502-1508 may include use of an immunochromatographic test strip to detect concentration of one or more analytes in stimulated saliva. A follow-up test may involve use of substantially the same test at a different point in time. A validation test may involve detection of concentration of one or more different analytes, and/or may involve detection of stimulated saliva production rate as disclosed previously herein. One skilled in the art with the benefit of the present disclosure will appreciate that any suitable types and/or number of tests may be performed over a selected time period.

FIG. 16 is a top plan view of a sampling portion 1600A of an apparatus for sensing hydration state or salivary secretion rate of a mammalian subject, the sampling portion 1600A including a liquid collection element 1610 arranged over a portion of a substrate 1630 having four sequentially arranged electrical contact pairs 1621A-1621D for sensing presence of saliva. Each electrical contact pair 1621A-1621D includes two contacts separated by a gap 1622A-1622D. The substrate 1630, which has a first end 1631-1 and a second end 1631-2, comprises a circuit board (e.g., FR4 material) with conductive electrical traces 1635 arranged on surfaces thereof. A protruding portion 1613 of the liquid collection element 1610 extends beyond the first end 1631-1 of the substrate 1630. Such portion 1613 may protrude approximately 5-10 mm beyond a substrate or housing. At least some electrical traces 1635 are in communication with interface contacts 1638 arranged for electrical connection to a monitoring portion of such an apparatus (e.g., such as monitoring portions shown in FIGS. 18-19). Although the substrate 1630 is shown as having exposed surfaces, in certain embodiments at least a portion of the substrate may be encased in a housing (not shown).

FIG. 17 is a top plan view of a portion of a sampling portion 1700A of another apparatus for sensing hydration state or salivary secretion rate of a mammalian subject, the sampling portion 1700A including a liquid collection element 1710 with a portion arranged on a substrate within a housing 1740, and with a protruding portion 1713 of the liquid collection element 1710 extending beyond a first end 1731-1 of the housing 1740. The housing 1740 includes a lengthwise ruler or numeric scale 1737 arranged to permit measurement of length of insertion of the housing 1740 into a mouth of a user and/or to permit visual observation of an extent of migration of saliva (although as shown in FIG. 17, the ruler or numeric scale 1737 extends well beyond the liquid collection element 1710. The ruler or scale 1737 may be desired since the desired length of insertion of a collection device may depend on the oral cavity size. Along a second end 1731-2 of the housing a socket 1739 is provided for receiving an interface cable for connecting to a monitoring portion of such an apparatus (e.g., such as monitoring portions shown in FIGS. 18-19). Although not shown, it is to be understood that the multiple electrical contact pairs or other sensing elements may be arranged on a substrate within the housing 1740 proximate to the liquid collection element 1710.

FIG. 18 illustrates a monitoring portion 1800B for use with a sampling portion as illustrated in FIG. 16 or FIG. 17. The monitoring portion 1800B includes an alphanumeric display 1850 such as may be used to output quantitative and/or qualitative information, and multiple other indicators 1851-1852 arranged to generate user-perceptible signals. The display 1850 and/or indicators 1851-1852 may be used to output signals indicative of operating status and/or test results.

FIG. 19 illustrates a monitoring portion 1900B for use with a sampling portion as illustrated in FIG. 16 or FIG. 17. The monitoring portion 1900B includes an alphanumeric display 1950 such as may be used to output quantitative and/or qualitative information, and multiple other indicators 1951-1953 arranged to generate user-perceptible signals. The monitoring portion 1900B further includes an interface cable 1958 arranged for coupling (e.g., in removable fashion) with a sampling portion.

FIGS. 20A-20C illustrate a sampling portion 2000A and a monitoring portion 2000B of an apparatus. The sampling portion 2000A includes a substrate 2030, a liquid collection element 2010 with a protruding portion 2013 extending beyond an end of the substrate 2030, electrical traces 2035-2036 provided on the substrate, and an interface connector 2038 arranged for removable connection to the monitoring portion 2000B. The monitoring portion 2000B includes a circuit board 2080, an alphanumeric display 2050, and processor 2090, and an interface socket 2059. As shown in FIG. 20C, the sampling portion 2000A may be coupled to the monitoring portion 2000B by way of the connector 2038 and the socket 2059. Other means of connecting the sampling portion 2000A and the monitoring portion 2000B could be employed, as disclosed previously herein.

FIGS. 21A-23B provide results of in vitro tests utilizing sampling portions according to FIG. 16 with liquid collection elements of three different compositions. In each instance a portion of the liquid collection element was placed in contact with a puddle of saliva arranged on a surface, and time for saliva to migrate from one electrical contact pair (or electrode) to the next (i.e., with electrical contact pair 1621A represented as "A", electrical contact pair 1621B represented as "B," and so on).

Figure 21B:
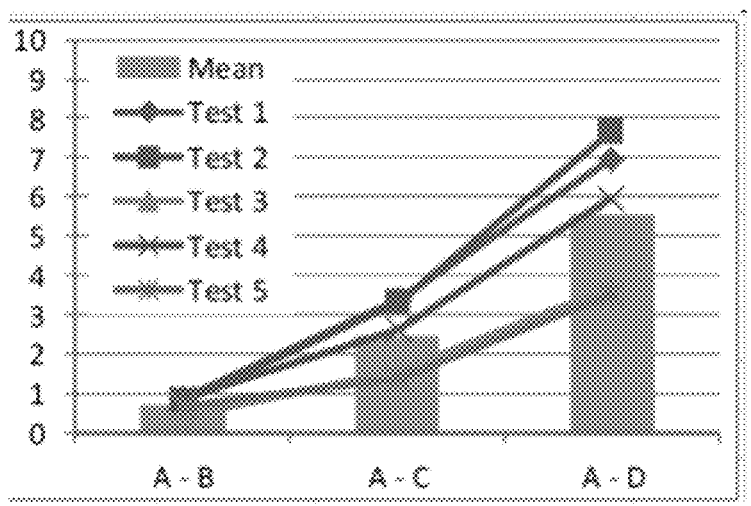
FIG. 21B is a line chart representing time for migration of saliva between respective electrodes of the salivary secretion rate sensing tests summarized in FIG. 21A, superimposed over a bar chart representing average migration times.

FIG. 21A is a table summarizing results of five salivary secretion rate sensing tests utilizing a sampling portion with a X5169 collection pad and four sequentially arranged electrical contact pairs A to D. FIG. 21B is a line chart representing time for migration of saliva between respective electrical contact pairs of the salivary secretion rate sensing tests summarized in FIG. 21A, superimposed over a bar chart representing average migration times.

Figure 22B:
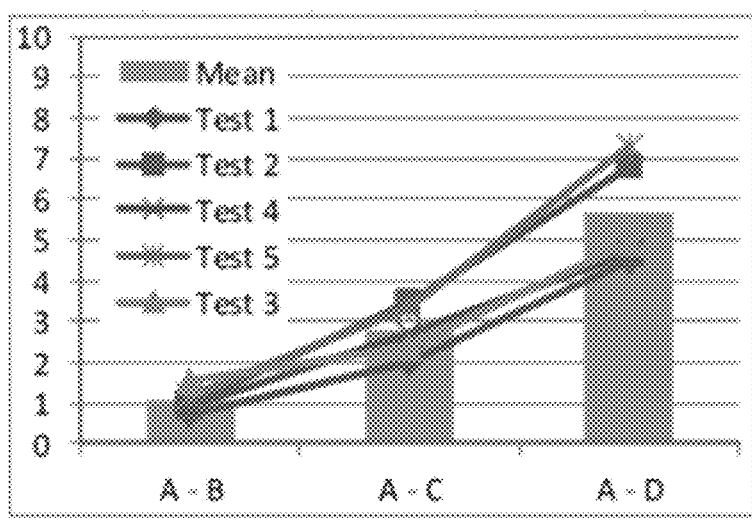
FIG. 22B is a line chart representing time for migration of saliva between respective electrodes of the salivary secretion rate sensing tests summarized in FIG. 22A, superimposed over a bar chart representing average migration times.

FIG. 22A is a table summarizing results of five salivary secretion rate sensing tests utilizing a sampling portion with a D4607 parallel collection pad and four sequentially arranged electrical contact pairs A to D. FIG. 22B is a line chart representing time for migration of saliva between respective electrical contact pairs of the salivary secretion rate sensing tests summarized in FIG. 22A, superimposed over a bar chart representing average migration times.

Figure 23B:
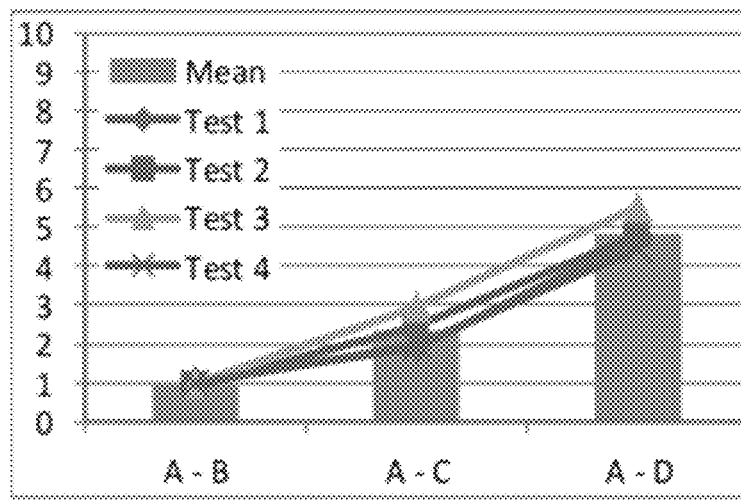
FIG. 23B is a line chart representing time for migration of saliva between respective electrodes of the salivary secretion rate sensing tests summarized in FIG. 23A, superimposed over a bar chart representing average migration times.

FIG. 23A is a table summarizing results of four salivary secretion rate sensing tests utilizing a sampling portion with a D4607 perpendicular collection pad and four sequentially arranged electrical contact pairs A to D. FIG. 23B is a line chart representing time for migration of saliva between respective electrical contact pairs of the salivary secretion rate sensing tests summarized in FIG. 23A, superimposed over a bar chart representing average migration times.

As shown in FIGS. 21B-23B, salivary migration time between the third and fourth electrode pair was slower than salivary migration time between the second and third electrode pair in each instance, despite the sequentially arranged electrode pairs being equidistantly spaced from one to the next.

FIG. 24A depicts a sampling portion 2400A of an apparatus for sensing hydration state or salivary secretion rate of a mammalian subject similar to the sampling portion illustrated in FIGS. 20A-20C, but with addition of two (circled) colored polymeric strips or loops 2419A-2419B as barriers or shielding elements extending over a protruding portion 2413 of the liquid collection element 2410. The liquid collection element 2410 is in the form of a D4607 perpendicular collection pad, and is arranged over four sequentially arranged electrical contact pairs A to D (as referenced in FIGS. 24B-24C). The liquid collection element 2410 is supported by a substrate 2430 having electrical traces 2435 and an electrical interface connector 2438. The barrier elements 2419A-2419B, which are spaced apart to expose portions of the liquid collection element therebetween, are generally liquid impermeable and are arranged to limit a tendency of an absorptive surface or portion of the liquid collection element from being restricted or blocked to further liquid flow (e.g., blocking by soft tissue below the tongue thereby sealing or restricting the liquid inlet within a subject's mouth). Presence of the barriers 2419A-2419B thereby prevents salivary flow restriction or stoppage.

FIG. 24B is a table providing results of three in vivo stimulated salivary secretion rate sensing tests utilizing the sampling portion of FIG. 24A. Saliva production was stimulated to rubbing 5 mg of powdered stimulant (55% citric acid, 45% sour candy) over the subject's tongue for 2 seconds. Twenty minutes elapsed between collections. FIG. 24C is a line chart representing time for migration of saliva between respective electrodes of the salivary secretion rate sensing tests summarized in FIG. 24B, superimposed over a bar chart representing average migration times. As shown in FIG. 24C, salivary migration time between the third and fourth electrode pair was closer to the salivary migration time between the second and third electrode pair than was the case in FIGS. 21B-23B.

FIG. 25A depicts a sampling portion 2500A of an apparatus for sensing hydration state or salivary secretion rate of a mammalian subject similar to the sampling portion illustrated in FIGS. 20A-20C, but with addition of a (circled) barrier or shielding element 2525 including two notches 2529A, 2529B defined therein and arrangeable over a protruding portion of a liquid collection element (not shown). The barrier or shielding element 2525 may be arranged to prevent blocking by soft tissue below the tongue thereby sealing or restricting the liquid inlet within a subject's mouth. A liquid collection element (not shown) may be arranged over four sequentially arranged electrical contact pairs (referenced as electrodes A to D in FIGS. 25B-25C). Such a liquid collection element may be supported by a substrate 2530 having electrical traces 2535 and an electrical interface connector 2538. The barrier or shielding element 2525 is generally liquid impermeable (e.g., constructed of polymeric material) and is arranged to limit a tendency of an absorptive surface or portion of the liquid collection element from being restricted or blocked to further liquid flow, thereby preventing salivary flow restriction or stoppage.

FIG. 25B is a table providing results of three in vivo stimulated salivary secretion rate sensing tests utilizing the sampling portion of FIG. 25A. Saliva production was stimulated to rubbing 5 mg of powdered stimulant (55% citric acid, 45% sour candy) over the subject's tongue for 2 seconds. Twenty minutes elapsed between collections. FIG. 25C is a line chart representing time for migration of saliva between respective electrodes of the salivary secretion rate sensing tests summarized in FIG. 25B, superimposed over a bar chart representing average migration times.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. An apparatus for sensing a state of euhydration, state of dehydration, or salivary secretion rate of a mammalian subject, the apparatus comprising:
a liquid collection element arranged for placement in fluid communication with oral mucosa of a mammalian subject, the liquid collection element being liquid-permeable, being arranged to transport liquid by wicking, and having a predefined liquid holding capacity;
a substrate arranged to support or engage the liquid collection element, with the substrate having arranged thereon a plurality of electrical contact pairs including a first electrical contact pair and a second electrical contact pair arranged downstream of the first electrical contact pair, wherein the first electrical contact pair is arranged to close a first electrical circuit upon exposure to saliva when the liquid collection element is placed in fluid communication with oral mucosa of the mammalian subject, and the second electrical contact pair is arranged to close a second electrical circuit upon exposure to saliva transported though at least a portion of the liquid collection element;
a timing element arranged to receive a signal indicative of closure of the first electrical circuit, arranged to receive a signal indicative of closure of the second electrical circuit, and arranged to generate a first time value indicative of time elapsed between the closure of the second electrical circuit and the closure of the first electrical circuit; and
a signaling element arranged to generate an output signal indicative of state of euhydration, state of dehydration, or salivary secretion rate of the mammalian subject based at least in part on the first time value.

2. An apparatus according to claim 1, wherein:
the plurality of electrical contact pairs includes third electrical contact pair arranged downstream of the second electrical contact pair, wherein the third electrical contact pair is arranged to close a third electrical circuit upon exposure to saliva transported by wicking though at least a portion of the liquid collection element;
the timing element is arranged to receive a signal indicative of closure of the third electrical circuit, and is arranged to generate a second time value indicative of time elapsed between the closure of the third electrical circuit and the closure of one of (a) the first electrical circuit and (b) the second electrical circuit; and
the signaling element is arranged to generate an output signal indicative of state of euhydration, state of dehydration, or salivary secretion rate of the mammalian subject based at least in part on the first time value and the second time value.

3. An apparatus according to claim 2, wherein:
the plurality of electrical contact pairs includes fourth electrical contact pair arranged downstream of the third electrical contact pair, wherein the fourth electrical contact pair is arranged to close a fourth electrical circuit upon exposure to saliva transported by wicking though at least a portion of the liquid collection element;
the timing element is arranged to receive a signal indicative of closure of the fourth electrical circuit, and is arranged to generate a third time value indicative of time elapsed between the closure of the fourth electrical circuit and the closure of one of (a) the first electrical circuit, (b), the second electrical circuit, and (c) the third electrical circuit; and
the signaling element arranged to generate an output signal indicative of state of euhydration, state of dehydration, or salivary secretion rate of the mammalian subject based at least in part on the first time value, the second time value, and the third time value.

4. An apparatus according to claim 1, comprising a removable cover arranged over at least a portion of the liquid collection element.

5. An apparatus according to claim 1, comprising an electrolyte arranged to increase conductivity of saliva collected by the liquid collection element.

6. An apparatus according to claim 1, wherein the liquid collection element comprises a porous medium or fibrous medium arranged to absorb saliva.

7. An apparatus according to claim 1, wherein the signaling element comprises a display.

8. An apparatus according to claim 1, including a processing element or comparator arranged to divide the predefined liquid holding volumetric capacity by the first time value to yield a volumetric salivary secretion rate, wherein the output signal comprises a user-perceptible quantitative signal indicative or correlative of the volumetric salivary secretion rate.

9. An apparatus according to claim 1, including a processing element or comparator arranged to compare at least one time value or at least one value obtainable from the at least one time value with at least one predefined threshold value, wherein the signaling element is arranged to generate a user-perceptible qualitative signal indicative of state of euhydration, state of dehydration, or salivary secretion rate based at least in part on such comparison.

10. An apparatus according to claim 2, including a processing element or comparator arranged to compare at least one of the time values with at least one other of the time values, wherein the signaling element is arranged to generate a user-perceptible qualitative signal indicative of state of euhydration, state of dehydration, or salivary secretion rate based at least in part on such comparison.

11. An apparatus according to claim 1, comprising a sampling portion and a monitoring portion, wherein the liquid collection element is arranged in the sampling portion, wherein each of the timing element and the signaling element is arranged in the monitoring portion, and wherein the sampling portion is operatively connected to the monitoring portion via at least one of an electrical communication cable, an electrical connector, and a wireless communication element.

12. An apparatus according to claim 1, comprising at least one indicator or test region arranged to interact with at least one analyte in saliva obtained from the mammalian subject, wherein the at least one indicator or test region is arranged in fluid communication with the liquid collection element.

13. An apparatus according to claim 12, wherein the at least one analyte comprises any of secretory IgA, albumin, secretory component, and aldosterone.

14. An apparatus according to claim 12, wherein the liquid collection element and the at least one indicator or test region are arranged in a sampling portion, each of the timing element and the signaling element is arranged in a monitoring portion, the sampling portion is removably insertable into a monitoring portion to establish electrical communication between the sampling portion and the monitoring portion, and the monitoring portion comprises an optical reading element arranged to sense an optical property of the at least one indicator or test region.

15. An apparatus according to claim 12, further comprising an optical reading element arranged to generate an electrical signal correlative of concentration of the at least one analyte upon optical interaction with the at least one indicator or test region.

16. An apparatus according to claim 15, further comprising a signal processing element arranged to utilize at least one time value in combination with the electrical signal correlative of concentration of the at least one analyte to generate an output signal indicative of state of euhydration, state of dehydration, or salivary secretion rate of the mammalian subject.

17. An apparatus according to claim 1, comprising a salivary stimulating agent arranged on or in at least a portion of the apparatus.

18. A kit comprising an apparatus according to claim 1 and a salivary stimulating agent arranged for placement into the mouth of the mammalian subject prior to or concurrently with placement of the at least a portion of the liquid collection element in fluid communication with oral mucosa of the mammalian subject.

19. A method utilizing the apparatus of claim 1 for sensing a state of euhydration, state of dehydration, or salivary secretion rate of a mammalian subject.

20. A method according to claim 19, further comprising use of the output signal to diagnose a disease state of the mammalian subject.

21. A method according to claim 20, wherein the disease state includes hyposalivation as a symptom thereof.

22. A method according to claim 20, wherein use of the output signal to diagnose a disease state comprises comparison of the output signal or information derived therefrom with at least one reference value or reference value range correlative of the disease state.

23. A method according to claim 19, further comprising use of the output signal to detect a side effect of drug interaction with the mammalian subject.

24. A method according to claim 23, wherein use of the output signal to detect a side effect of drug interaction comprises comparison of the output signal or information derived therefrom with at least one reference value or reference value range correlative of the side effect of drug interaction.

25. A method according to claim 23, further comprising adjusting dosage or administration of a drug responsive to the detection of a side effect of drug interaction.

26. An apparatus for sensing a state of euhydration, state of dehydration, or salivary secretion rate of a mammalian subject, the apparatus comprising:
   a liquid collection element arranged for placement in fluid communication with oral mucosa in the mouth of a mammalian subject, the liquid collection element being liquid permeable, being arranged to transport liquid by wicking, and having a predefined liquid holding capacity;
   a salivary stimulating agent arranged for placement into the mouth of the mammalian subject prior to or concurrently with placement of the at least a portion of the liquid collection element in fluid communication with oral mucosa of the mammalian subject;
   at least one first electrode or sensing element arranged to sense a condition indicative of exposure of a portion of the liquid collection element to oral mucosa in the mouth of a mammalian subject;
   at least one second electrode or sensing element arranged to sense a condition indicative of movement by saliva through at least a portion of the liquid collection element;
   a timing element arranged to be initiated responsive to receipt of a signal from or detection of change of state of the at least one first electrode or sensing element, and to generate a time value indicative of elapsed time since said initiation upon receipt of a signal from or detection of a change of state of the at least one second electrode or sensing element; and
   a signaling element arranged to generate an output signal indicative of state of euhydration, state of dehydration, or salivary secretion rate of the mammalian subject based at least in part on the time value.

* * * * *